(12) United States Patent
Song et al.

(10) Patent No.: US 11,564,990 B2
(45) Date of Patent: Jan. 31, 2023

(54) MULTI-DRUG-LOADING-SITE, HIGH DRUG-LOADING CAPACITY LIGAND-DRUG CONJUGATE

(71) Applicant: JenKem Technology Co., Ltd. (Beijing), Beijing (CN)

(72) Inventors: Yanping Song, Beijing (CN); Jinghui Du, Beijing (CN); Leimin Wang, Beijing (CN); Jinliang Wang, Beijing (CN); Meina Lin, Beijing (CN); Zewang Feng, Beijing (CN); Xuan Zhao, Beijing (CN)

(73) Assignee: JENKEM TECHNOLOGY CO., LTD. (BEIJING), Beijing (CN)

( * ) Notice: Subject to any disclaimer, the term of this patent is extended or adjusted under 35 U.S.C. 154(b) by 103 days.

(21) Appl. No.: 16/588,010

(22) Filed: Sep. 30, 2019

(65) Prior Publication Data
US 2020/0046842 A1 Feb. 13, 2020

Related U.S. Application Data

(63) Continuation of application No. PCT/CN2018/080680, filed on Mar. 27, 2018.

(30) Foreign Application Priority Data

Mar. 29, 2017 (CN) .......................... 201710197518.2

(51) Int. Cl.
| | |
|---|---|
| *A61K 47/60* | (2017.01) |
| *A61K 31/436* | (2006.01) |
| *A61K 47/65* | (2017.01) |
| *A61K 47/68* | (2017.01) |

(52) U.S. Cl.
CPC ............ *A61K 47/60* (2017.08); *A61K 31/436* (2013.01); *A61K 47/65* (2017.08); *A61K 47/6803* (2017.08); *A61K 47/6883* (2017.08)

(58) Field of Classification Search
None
See application file for complete search history.

(56) References Cited

U.S. PATENT DOCUMENTS

| | | | |
|---|---|---|---|
| 2003/0026764 A1* | 2/2003 | Griffiths | A61K 47/646 424/9.34 |
| 2014/0349945 A1* | 11/2014 | Xu | A61K 47/60 514/19.3 |

FOREIGN PATENT DOCUMENTS

| | | | |
|---|---|---|---|
| CN | 1995094 | * | 7/2007 |
| EP | 3466976 | * | 4/2019 |

* cited by examiner

*Primary Examiner* — Tigabu Kassa
(74) *Attorney, Agent, or Firm* — Flener IP & Business Law; Zareefa B. Flener

(57) ABSTRACT

The present invention provides a multi-drug-loading site and high drug-loading capacity ligand-drug conjugate. The ligand-drug conjugate has a structure of general formula (I). The ligand-drug conjugate has the characteristics of high loading capacity, high drug efficacy, low toxicity, and low risks. The ligand-drug conjugate can be used particularly to connect to a low toxicity chemical molecule, thereby extending a therapeutic window. Furthermore, the present invention provides an antibody-drug conjugate molecule. The antibody-drug conjugate molecule has the characteristics of multiple drug-loading ability and high drug-loading capacity, such that the antibody-drug conjugate can carry a large amount of a low toxicity chemical molecule and achieve a therapeutic effect without depending on antibody targeting or high toxicity chemicals.

$$TM\text{-}\{R^2\text{-}PEG1\text{-}[R^1\text{-}PEG2\text{-}(R^3\text{-}A'\text{-}D)_n]_m\}_l \quad (I)$$

5 Claims, 2 Drawing Sheets

MULTI-DRUG-LOADING-SITE, HIGH DRUG-LOADING CAPACITY LIGAND-DRUG CONJUGATE

CROSS-REFERENCE TO RELATED APPLICATION

This application is a continuation application of International patent application No. PCT/CN2018/080680, filed on Mar. 27, 2018, which claims the benefit and priority of Chinese patent application No. CN201710197518.2, filed on Mar. 29, 2017, each of which is incorporated herein by reference in its entirety and for all purposes.

FIELD OF THE INVENTION

The invention relates to the technical field of medicine, in particular to a multi-drug-loading site, high drug-loading capacity ligand-drug conjugate and a pharmaceutical composition thereof, and a preparation method and the use thereof.

BACKGROUND OF THE INVENTION

Antibody-Drug Conjugates (ADC) is a conjugating product formed by coupling a monoclonal antibody (Monoclonal Antibody, mAb) to a biologically active small molecule drug through a linker. It can "accurately" deliver the small molecule drug to the tumor cells by use of the characteristics through which the antibody specifically recognizes the tumor cell, increasing the drug concentration at the tumor site while reducing the drug concentration at normal tissues and organs, thereby achieving an anti-tumor effect with high efficiency and low toxicity. The first antibody-drug conjugate, gemtuzumab ozogamicin (Mylotarg®), was approved by US FDA in 2000. Although the drug was withdrawn after 10 years due to safety concerns, brentuximab vedotin (SGN-35, Adcetris®) was approved for the treatment of Hodgkin's lymphoma, and anaplastic large cell lymphoma by US FDA and the European Medicines Agency in 2011, and trastuzumab emtansine (T-DMI, Kadcyla®) was approved for the treatment of HER-2 positive breast cancer in 2013. Both the ADCs have achieved exciting therapeutic effects. At present, there are more than 50 kinds of ADCs in the clinical research stage, and ADCs have become an important new anti-tumor drugs.

Although the development of new ADC drugs has achieved unprecedented success, the technology still needs further optimization. Most of the coupling agents in the ADC are short-chain rigid hydrophobic molecules, which also have a certain effect on the water solubility and immunogenicity of the drug itself. In addition, most of the drugs in the ADC are hydrophobic, which may cause problems due to aggregation after the hydrophobic drug is attached to the antibody. The aggregates do not dissolve, which in turn affects the drug loading. Studies have shown that ADC aggregates accumulate in the liver, causing hepatotoxicity (Jarvis L M, Jarvis L M. Rethinking Antibody-Drug Conjugates [J]. Chem. eng. news, 2013, 90(25)). Finally, protein aggregation of biological formulation generally causes immunogenicity (Joubert M K, Hokom M, Eakin C, et al. Highly Aggregated Antibody Therapeutics Can Enhance the in Vitro Innate and Late-stage T-cell Immune Responses [J]. Journal of Biological Chemistry, 2012, 287(30): 25266-25279).

Patent document CN201510160703.5 discloses an antibody-drug conjugate obtained by covalently coupling a drug molecule and a Fab' fragment to a heterobifunctional polyethylene glycol. Although the above antibody conjugate has a determined drug-loaded point and an exact drug loading ratio, the drug loading point is only a few, which is not favorable to increasing the drug loading of the whole conjugate.

SUMMARY OF THE INVENTION

By using the PEG linker in the ligand drug conjugates, the inventors of the present invention can achieve the effect of masking the hydrophobicity of the drug or the coupling agent, avoiding the aggregation and precipitation of the conjugate. In addition, there are more drug loading points in the conjugates, so that the conjugates can carry more drugs while maintaining a consistent other characteristics such as pharmacokinetics with low drug loading conjugates. In addition, when compared to another long-acting drug, PEG-Drug, the ligand drug conjugate has a significantly superior half-life than that of PEG-Drug. Thus it provide an alternative to long-acting carrier.

In one aspect, the invention provides a ligand drug conjugate having a structure represented by general formula I:

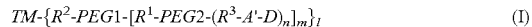

$$TM-\{R^2-PEG1-[R^1-PEG2-(R^3-A'-D)_n]_m\}_l \qquad (I)$$

wherein:

TM is a ligand unit;

PEG1 and PEG2 are the same or different polyethylene glycol residues;

l is an integer from 11 to 500;

m is an integer from 1 to 7;

n is an integer from 1 to 7;

A' is a spacer which is optionally present;

$R^1$ is a linking unit linking PEG1 and PEG2;

$R^2$ is a ligand unit linking the ligand unit and PEG1;

$R^3$ is a linking unit linking PEG2 and spacer A' or a drug; and

D is a drug.

In Formula I, l is an integer from 11 to 500 (such as 11, 20, 30, 40, 50, 60, 70, 80, 90, 100, 150, 200, 250, 300, 350, 400, 450 or 500). Preferably, l is an integer from 11 to 100, and more preferably, the l is an integer from 11 to 50.

When l is 11, any of the 11 linking sites of the ligand unit are respectively linked to a PEG linker.

In an embodiment of the invention, one PEG linker can couple from 1 to 49 drug molecules.

For example, when m is 1 and n is 1, one drug molecule is coupled; when m is 1 and n is 2, two drug molecules are coupled; when m is 2 and n is 2, 4 drug molecules are coupled Drug molecule; when m is 2 and n is 3, 6 drug molecules are coupled; when m is 3 and n is 3, 9 drug molecules are coupled; when m is 3 and n is 7, 21 drug molecules are coupled; when m is 7 and n is 7, 49 drug molecules are coupled.

When two PEG linkers are present in the ligand drug conjugate, 2 to 98 drug molecules can be coupled.

When three PEG linkers are present in the ligand drug conjugate, the ligand drug conjugate can couple 3 to 147 drug molecules, and so on. The ligand drug conjugate of the present invention have more drug-loading points, and thus can greatly increase the amount of drug loading.

In Formula I, e m is 1, 2, 3, 4, 5, 6, or 7.

In one embodiment of the invention, m is 1, 3, 5 or 7.

In a preferred embodiment of the invention, m is 1 or 3.

In Formula I, n is 1, 2, 3, 4, 5, 6, or 7.

In one embodiment of the invention, n is 1, 3, 5 or 7.

In a preferred embodiment of the invention, n is 1 or 3.

In an embodiment of the present invention, in the ligand drug conjugate, the TM ligand unit is a disease targeting unit; preferably, the disease targeting unit is an antibody, wherein the antibody comprises a monoclonal antibody a polyclonal antibody, preferably a monoclonal antibody; in the present invention, the antibody may be in a form selected from the group consisting of a chimeric antibody, a humanized antibody, a fully human antibody, and an antibody fragment capable of binding to an antigen (Fab, Fab', F(ab)$_2$, F(ab')$_2$), a subfragment (single-stranded construct) or an antibody Fc fusion protein.

In a specific embodiment of the present invention, preferably, the monoclonal antibody is reactive against an antigen associated with cancer, malignant cells, infectious organisms or autoimmune diseases or an epitope thereof.

In a specific embodiment of the present invention, preferably, the monoclonal antibody is selected from the group consisting of: anti-HER2 antibody, anti-EGFR antibody, anti-PMSA antibody, anti-VEGFR antibody, anti-CD30 antibody, anti-CD22 antibody, anti-CD56 antibody, anti-CD29 antibody, anti-GPNMB antibody, anti-CD138 antibody, anti-CD74 antibody, anti-ENPP3 antibody, anti-Nectin-4 antibody, anti-EGFRVIII antibody, anti-SLC44A4 antibody, anti-mesothelin antibody (anti-mesothelin antibody), anti-ET8R antibody, anti-CD37 antibody, Anti-CEACAM5 antibody, anti-CD70 antibody, anti-MUC16 antibody, anti-CD79b antibody, anti-MUC16 antibody and anti-Muc1 antibody.

In one embodiment of the invention, the monoclonal antibody is an anti-HER2 antibody.

In a preferred embodiment of the invention, the anti-HER2 antibody is a recombinant anti-HER2 humanized monoclonal antibody.

In a specific embodiment of the present invention, preferably, the antigen is selected from the group consisting of: HER-2/neu, carbonic anhydrase IX, B7, CCCL19, CCCL21, CSAp, BrE3, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF, ED-B fibrosis protein, EGP-1, EGP-2, EGF receptor (ErbB1), ErbB2, ErbB3, factor H, FHL-1, Flt-3, folate receptor, Ga733, GROB, HMGB-1, hypoxia-inducible factor (HIF)), HM1.24, insulin-like growth factor (ILGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, Ganglioside, HCG, HLA-DR, CD66a-d, MAGE, mCRP, MCP-1, MIP-1A, MIP-1B, macrophage migration inhibition Subunit (MIF), MUC1, MUC2, MUC3, MUC4, MUC5, placental growth factor (PIGF), PSA, PSMA, PSMA dimer, PAM4 antigen, NCA-95, NCA-90, A3, A33, Ep-CAM, KS-1, Le(y), mesothelin, S100, tenascin, TAC, Tn antigen, Thomas-Friedenreich antigen, tumor necrosis antigen, tumor angiogenic antigen, TNF-α, TRAIL receptor (R1 and R2), VEGFR, RANTES, T101, cancer stem cell antigen, complement factor C3, C3a, C3b, C5a, C5 and oncogene products.

In an embodiment of the present invention, in the ligand drug conjugate, the A' is selected from the group consisting of: a chemically labile linker (such as a hydrazone and a disulfide linker), and an enzyme-catalyzed linker (such as a peptide linker, a β-glucuronide linker, an esterase-labile carbonate linker) and one or more identical or different amino acid residues or derivatives thereof; the amino acid is selected from the group consisting of: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In one embodiment of the present invention, when the drug is a polypeptide or a protein drug, the A' may be a single bond, and $R^3$ is directly linked to the polypeptide or the protein drug.

In a specific embodiment of the present invention, preferably, the A' is one or more selected from the group consisting of: a single bond, a carbonate residue, an amino acid ester residue, a β-glucuronide residue, or one or more identical or different amino acid residues or a derivative thereof.

In a specific embodiment of the invention, the amino acid is one or more selected from the group consisting of: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; preferably, the amino acid is selected from one or more of aspartic acid, glutamic acid, glycine, isoleucine, leucine, phenylalanine, and valine.

In a specific embodiment of the present invention, preferably, the A' is one or more selected from the group consisting of: a single bond, a glycine ester bond, a carbonate residue, a β-glucuronide residue, a valine residue, a glycine residue, a aspartic-valine residue and a glutamate-valine residue.

In one embodiment of the invention, the A' is a valine residue.

In another embodiment of the invention, said A' is a single bond.

In a specific embodiment of the present invention, in the ligand drug conjugate, the linking unit $R^1$ linking PEG1 and PEG2 has a structure of -A$_1$-B-A$_2$-, wherein A$_1$ and A$_2$ are independently selected from the group consisting of: —(CH$_2$)$_i$—, —(CH$_2$)$_i$O—, —(CH$_2$)$_i$NH—, —(CH$_2$)$_i$CO—, —(CH$_2$)$_i$OCOO—, —(CH$_2$)$_i$OCONH—, —(CH$_2$)$_i$NHCONH—, —(CH$_2$)$_i$NHCO—, —O(CH$_2$)$_i$COO—, —(CH$_2$)$_i$COO—, and —(CH$_2$)$_i$CONH—, or the combination thereof, i is an integer from 0 to 10; preferably, i is 0, 1, or 2;

B is a thiol reactive group, and the reactive end groups of the reaction are independently selected from the group consisting of: a sulfhydryl group, a sulfhydryl reactive group; the thiol reactive group can react with thiol to produce thioether bonding or disulfide. It comprises, but not limited to, maleimide group, glutaric acid group, a vinylsulfone group, a haloacetamide group, a pyridyl disulfide group, a thiosulfonate group, an ethylene imine group, an aziridine group, and an aminosulfonyl group. The reactive end groups are preferably selected from the group consisting of: a sulfhydryl group, a maleimide group, a vinylsulfone group, and a haloacetylamino group.

In one embodiment of the invention, A$_1$ has a structure of: —CH$_2$CH$_2$NHCOCH$_2$CH$_2$— or —OCH$_2$—.

In one embodiment of the invention, A$_2$ has a structure of: —CH$_2$CH$_2$— or —CH$_2$CH$_2$O—.

In a preferred embodiment of the invention, B has a structure of:

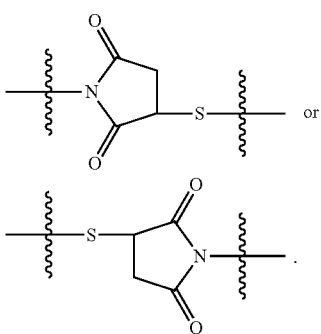

In another embodiment of the present invention, in the ligand drug conjugate, another form of the linking unit $R^1$ linking PEG1 and PEG2 is obtained by a click reaction, and the reactive end groups at which the click reaction occurs are azido and alkynyl groups, respectively.

In another preferred embodiment of the invention, B has a structure of:

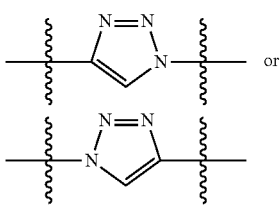

In a specific embodiment of the invention, $R^1$ has a structure of:

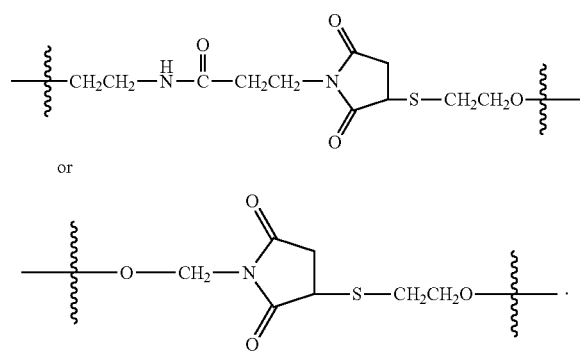

In an embodiment of the present invention, in the ligand drug conjugate, the coupling unit $R^2$ linking the linking ligand unit and PEG1 is selected from the group consisting of: —$(CH_2)_i$—, —$(CH_2)_i$NH—, —$(CH_2)_i$CO—, —$(CH_2)_i$OCOO—, —$(CH_2)_i$OCONH—, —$(CH_2)$ NHCONH—, —$(CH_2)_i$NHCO—, —OC$(CH_2)_i$COO—, —$(CH_2)_i$COO— and —$(CH_2)_i$CONH, or the combination thereof, i is an integer from 0 to 10; preferably, i is 0, 1, or 2.

In one embodiment of the invention, $R^2$ has a structure of: —NHCOCH$_2$—.

In a specific embodiment of the present invention, in the ligand drug conjugate, the coupling unit $R^2$ linking the ligand unit and PEG1 forms an amide bond by combining the amino group of the ligand unit with the reactive end group of PEG1, and is selected from the group consisting of succinimidyl succinate (SS), succinimidyl carbonate (SC), mPEG-imidate (mPEG-imidate), para-nitrophenylcarbonate (NPC), succinimidyl propionate (SPA) and cyanuric chloride.

It is known to those skilled in the art that common groups on the ligand unit which can react with PEG1 further include: —NH—, —OH, —SH, —COOH, as well as the guanidino of arginine, the imidazolyl group of histidine and the glycosyl group of glycoprotein (containing an aldehyde group, a hydroxyl group, a primary amino group, a carboxyl group, a phosphate group, etc.).

In an embodiment of the present invention, in the ligand drug conjugate, the linking unit $R^3$ linking PEG2 and the spacer A' or the drug is selected from the group consisting of: —$(CH_2)_i$OCOO—, —$(CH_2)_i$OCONH—, —$(CH_2)_i$NHCONH—, —$(CH_2)_i$NHCO—, —OC$(CH_2)_i$COO—, —$(CH_2)_i$COO—, —$(CH_2)_i$CONH— and —$(CH_2)_i$CO—, or the combination thereof, i is an integer from 0 to 10; preferably, i is 0, 1, or 2.

In one embodiment of the invention, the $R^3$ has a structure as follows of: —CH$_2$CO—.

In one embodiment of the present invention, in the ligand drug conjugate, the drug is an antitumor drug, including but not limited to one or more of: irinotecan, topotecan, belotecan, exatecan, lurtotecan, diflomotecan, gimatecan, karenitecin, doxorubicin (DOX), epirubicin, morpholinodoxorubicin, cyanomorpholinodoxorubicin, 2-pyrrolinyl doxorubicin, camptothecin (CPT), 10-hydroxycamptothecin, SN-38, 9-aminocamptothecin, 9-nitrocamptothecin, taxane, geldanamycin, ansamycin and epothilone.

In another embodiment of the present invention, in the ligand drug conjugate, the drug is an anti-tumor polypeptide (eg, "Zhang Wei, Lao Xingzhen, Zheng Zheng. Research progress in anti-tumor small molecule peptides [J]. Amino Acids and Biological Resources, 2012, 34(4): 42-46"), including but not limited to one or more of: thymopentin, octreotide, RGD peptide, tyroserleutide, tyroservatide, YIGSR peptide, ND100, TZT-1027 and BuforinIIb.

In a specific embodiment of the present invention, the ligand drug conjugate, the drug is one or more selected from the group consisting of: irinotecan, topotecan, belotecan, exatecan, lurtotecan, diflomotecan, gimatecan, karenitecin, camptothecin (CPT), 10-hydroxycamptothecin, SN-38, 9-aminocamptothecin and 9-nitrocamptothecin.

In a specific embodiment of the present invention, the ligand drug conjugate, the drug is one or more selected from the group consisting of: thymopentin, octreotide, RGD peptide, tyroserleutide, tyroservatide, YIGSR peptide, and ND100.

In one embodiment of the invention, the drug is irinotecan.

In one embodiment of the invention, the drug is tyroservatide (YSV).

In one embodiment of the invention, when the drug is an anti-tumor polypeptide, the A' may be a single bond, and the $R^3$ is directly linked to the anti-tumor polypeptide.

In a specific embodiment of the present invention, preferably, in the ligand drug conjugate, the drug is a low toxicity drug. Specifically, when the drug is a low toxicity drug, the ligand drug conjugate contains more drug molecules.

In an embodiment of the invention, in the ligand drug conjugate, the PEG1 is a defined polyethylene glycol residue having 1-960 monomer units, preferably a defined polyethylene glycol residue having 1-480 monomer units, more preferably a defined polyethylene glycol residue having 1-240 monomer units, further preferably a defined polyethylene glycol residue having from 1-120 monomer units.

In an embodiment of the present invention, in the ligand drug conjugate, the PEG1 is a linear, Y-type or multi-branched polyethylene glycol residue, for example, including a linear double-end PEG, a Y-type PEG, 4-arm branched PEG, 6-arm branched PEG or 8-arm branched PEG, etc, preferably Y-type or multi-branched polyethylene glycol residues.

The PEG has a molecular weight of 1 to 100 KDa, for example, 1 to 20 KDa (specifically, 1, 2, 3, 4, 5, 6, 7, 8, 9, 10, 11, 12, 13, 14, 15, 16, 17, 18, 19 or 20 KDa), 20 to 50 KDa (specifically 20, 25, 30, 35, 40, 45 or 50 KDa) or 50 to 100 KDa (specifically 50, 55, 60, 65, 70, 75, 80, 85, 90, 95 or 100 KDa), etc.; preferably, the PEG has a molecular weight of 1 to 20 KDa, more preferably 1 to 10 KDa, for example 1 to 5 KDa or 5 to 10 KDa.

In a specific embodiment of the present invention, the PEG1 is a linear polyethylene glycol residue having a structure represented by formula III-1:

(III-1)

wherein p1 is an integer from 1 to 960, preferably an integer from 1 to 480, more preferably an integer from 1 to 240, still more preferably an integer from 1 to 120.

In a specific embodiment of the present invention, the PEG1 is a Y-type polyethylene glycol residue having a structure represented by formula IV-1:

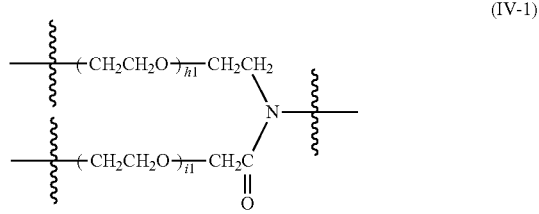

(IV-1)

wherein h1 and i1 are independently selected from an integer from 1 to 480, preferably from an integer from 1 to 240, more preferably from an integer from 1 to 120, further preferably from an integer from 1 to 60.

In a specific embodiment of the present invention, the PEG1 is a multi-branched polyethylene glycol residue having a structure represented by formula V-1:

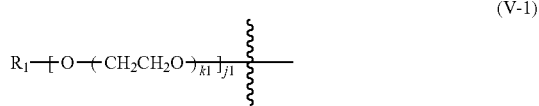

(V-1)

wherein k1 is an integer from 1 to 240, preferably an integer from 1 to 120, more preferably an integer from 1 to 80, further preferably an integer from 1 to 40;
j1 is an integer from 3-8 (eg, 3, 4, 5, 6, 7, 8);
$R_1$ is a core molecule of a multi-branched polyethylene glycol, and $R_1$ is selected from the group consisting of residues of pentaerythritol, oligo-pentaerythritol, methyl glucoside, sucrose, diethylene glycol, propylene glycol, glycerin, and polyglycerin; preferably, $R_1$ is selected from: pentaerythritol, dipentaerythritol and tripentaerythritol.

In one embodiment of the invention, the multi-branched polyethylene glycol residue has a structure of:

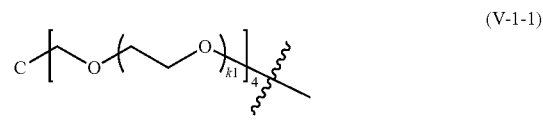

(V-1-1)

wherein k1 is an integer from 1 to 240, preferably an integer from 1 to 120, more preferably an integer from 1 to 80, still more preferably an integer from 1 to 40.

In an embodiment of the invention, in the ligand drug conjugate, the PEG2 is a defined polyethylene glycol residue having 1-960 monomer units, preferably a defined polyethylene glycol residue having 1-480 monomer unit, more preferably a defined polyethylene glycol residue having 1-240 monomer units, further preferably a defined polyethylene glycol residue having 1-120 monomer units.

In an embodiment of the present invention, in the ligand drug conjugate, the PEG2 is a linear, Y-type or multi-branched polyethylene glycol residue, for example, including a linear double-end PEG, a Y-type PEG, 4-arm branched PEG, 6-arm branched PEG or 8-arm branched PEG, etc., preferably Y-type or multi-branched polyethylene glycol residues.

The PEG has a molecular weight of 1 to 100 KDa, for example, 1 to 20 KDa (specifically, 1, 2, 3, 4, 5, 6, 7, 8, 9, 10, 11, 12, 13, 14, 15, 16, 17, 18, 19 or 20 KDa), 20 to 50 KDa (specifically 20, 25, 30, 35, 40, 45 or 50 KDa) or 50 to 100 KDa (specifically 50, 55, 60, 65, 70, 75, 80, 85, 90, 95 or 100 KDa), etc.; preferably, the PEG has a molecular weight of 1 to 20 KDa, more preferably 1 to 10 KDa, for example 1 to 5 KDa or 5 to 10 KDa.

In a specific embodiment of the invention, the PEG2 is a linear polyethylene glycol residue having a structure of formula III-2:

(III-2)

wherein $p^2$ is an integer from 1 to 960, preferably an integer from 1 to 480, more preferably an integer from 1 to 240, still more preferably an integer from 1 to 120.

In a specific embodiment of the present invention, the PEG2 is a Y-type polyethylene glycol residue having a structure of formula IV-2:

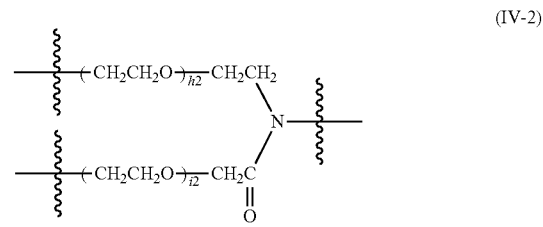

(IV-2)

wherein h2 and i2 are independently selected from an integer from 1 to 480, preferably from an integer from 1 to 240, more preferably from an integer from 1 to 120, further preferably from an integer from 1 to 60.

In a specific embodiment of the present invention, the PEG2 is a multi-branched polyethylene glycol residue having a structure of the formula V-2:

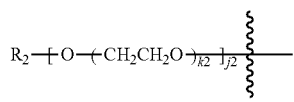

(V-2)

wherein k2 is an integer from 1 to 240, preferably an integer from 1 to 120, more preferably an integer from 1 to 80, further preferably an integer from 1 to 40;

j2 is an integer of 3-8 (such as 3, 4, 5, 6, 7, 8);

$R_2$ is a core molecule of a multi-branched polyethylene glycol, and $R_2$ is selected from the group consisting of residues of pentaerythritol, oligo-pentaerythritol, methyl glucoside, sucrose, diethylene glycol, propylene glycol, glycerin, and polyglycerin; preferably, the $R_2$ is selected from: pentaerythritol, dipentaerythritol and tripentaerythritol.

X is

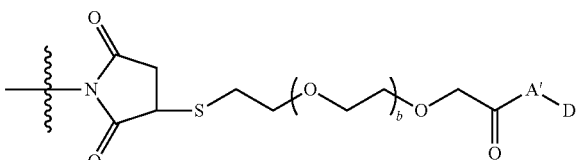

wherein, TM is a ligand unit, A' is a spacer, D is a drug, and a is selected from an integer of 1 to 960, preferably an integer from 1 to 480, more preferably an integer from 1 to 420, further preferably from 1 to 120; b is selected from an integer from 1 to 480, preferably from 1 to 240, more preferably from 1 to 120, further preferably from 1 to 60. The TM, A' and D have the above definitions of the invention.

In a preferred embodiment of the invention, in the above formula VI, the TM is an anti-HER2 monoclonal antibody, preferably a recombinant anti-HER2 humanized monoclonal antibody.

In one embodiment of the invention, in the above VI, the A' is a Valine residue.

In an embodiment of the present invention, in the above VI, -A'-D has a structure of:

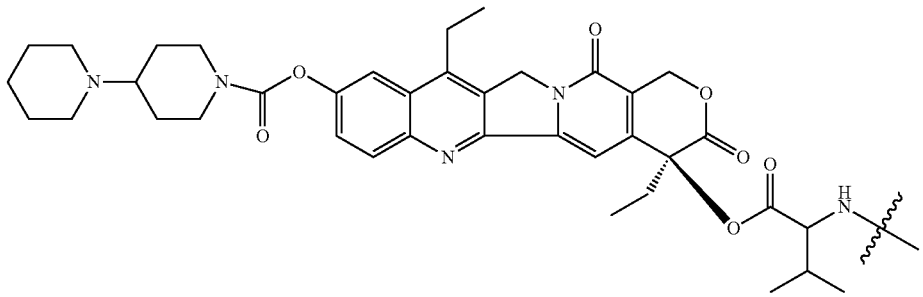 [SMILES: *NC(C(=O)O[C@]1(CC)C(=O)OCc2c1cc1n(c2=O)Cc2c-1nc1ccc(OC(=O)N3CCC(N4CCCCC4)CC3)cc1c2CC)C(C)C]

In one embodiment of the invention, the multi-branched polyethylene glycol residue has a structure of:

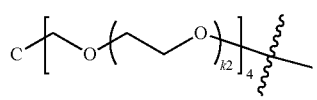

(V-2-1)

Wherein k2 is an integer from 1 to 240, preferably an integer from 1 to 120, more preferably an integer from 1 to 80, still more preferably an integer from 1 to 40.

In a preferred embodiment of the invention, the ligand drug conjugate has a structure represented by Formula VI:

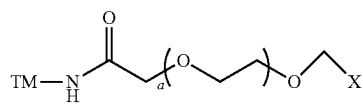

(VI)

In still another embodiment of the present invention, in the above VI, the A' is a single bond.

In another embodiment of the present invention, in the above VI, -A'-D has a structure of:

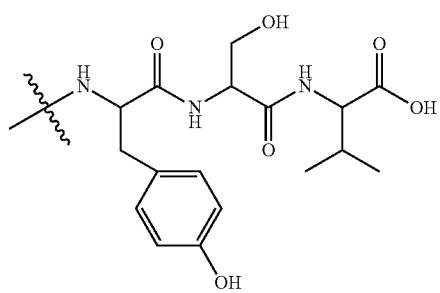 [SMILES: *NC(Cc1ccc(O)cc1)C(=O)NC(CO)C(=O)NC(C(=O)O)C(C)C]

In another preferred embodiment of the invention, the ligand drug conjugate has a structure represented by Formula VII:

(VII)

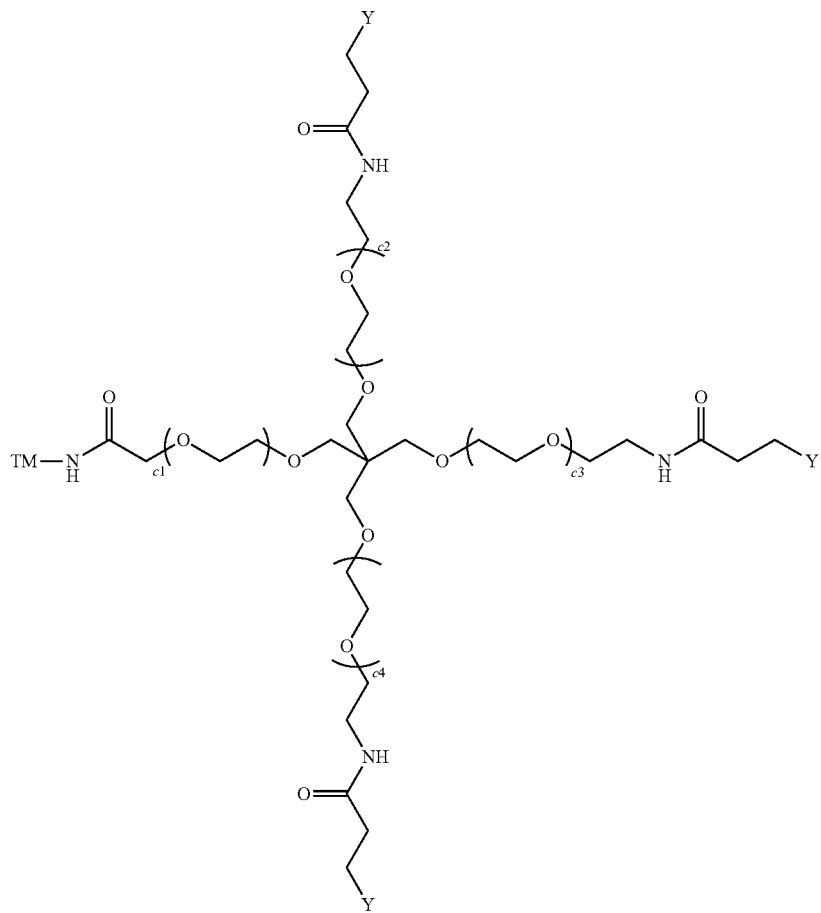

Y is

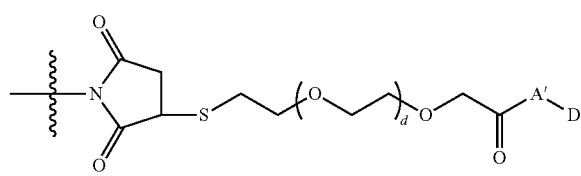

wherein TM is a ligand unit, A' is a spacer, D is a drug, and c1 to c4 is independently selected from an integer from 1 to 240, preferably from an integer from 1 to 120, more preferably from an integer from 1 to 80, further preferably an integer from 1 to 40; d is an integer d from 1 to 480, preferably an integer from 1 to 420, more preferably an integer from 1 to 120, further preferably an integer from 1 to 60. The TM, A' and D have the above definitions of the invention.

In a preferred embodiment of the invention, in the above formula VII, the c1 to c4 is an equal integer.

In a preferred embodiment of the invention, in the above formula VII, the TM is an anti-HER2 monoclonal antibody, preferably a recombinant anti-HER2 humanized monoclonal antibody.

In one embodiment of the invention, in the above formula VII, the A' is a Valine residue.

In an embodiment of the invention, in the above VI, the -A'-D has a structure of:

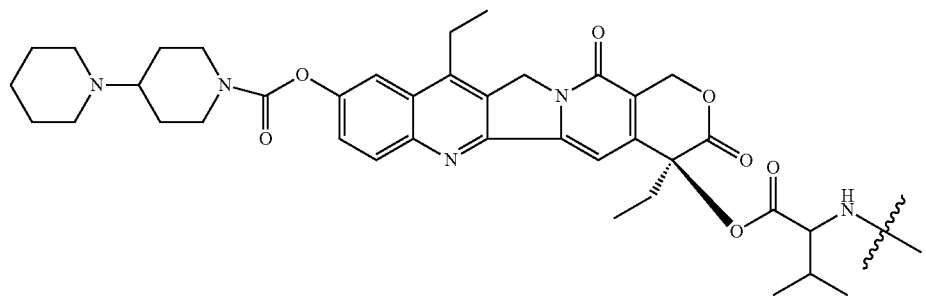 [SMILES: *NC(C(=O)O[C@]1(CC)C(=O)OCc2c1cc1n(c2=O)Cc2c-1nc1ccc(OC(=O)N3CCC(N4CCCCC4)CC3)cc1c2CC)C(C)C]

In still another embodiment of the present invention, in the above formula VII, A' is a single bond.
In another embodiment of the present invention, in the above VII, -A'-D has a structure of:
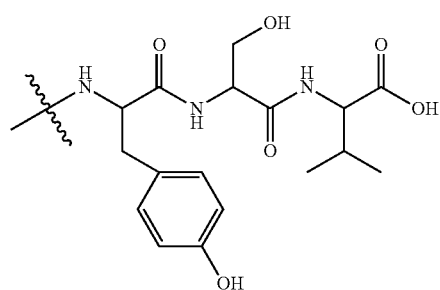 [SMILES: *NC(Cc1ccc(O)cc1)C(=O)NC(CO)C(=O)NC(C(=O)O)C(C)C]
In another preferred embodiment of the invention, the ligand drug conjugate has a structure represent by Formula VIII:
(VIII)
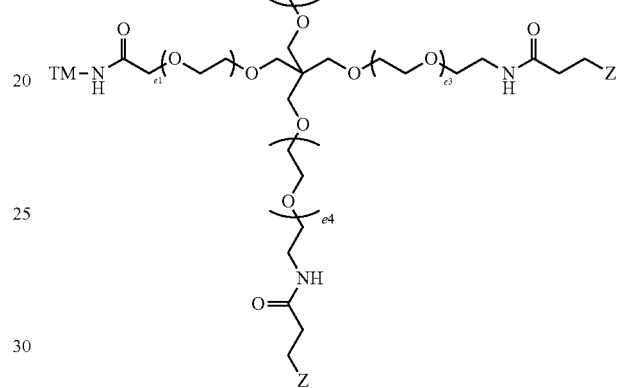
Z is
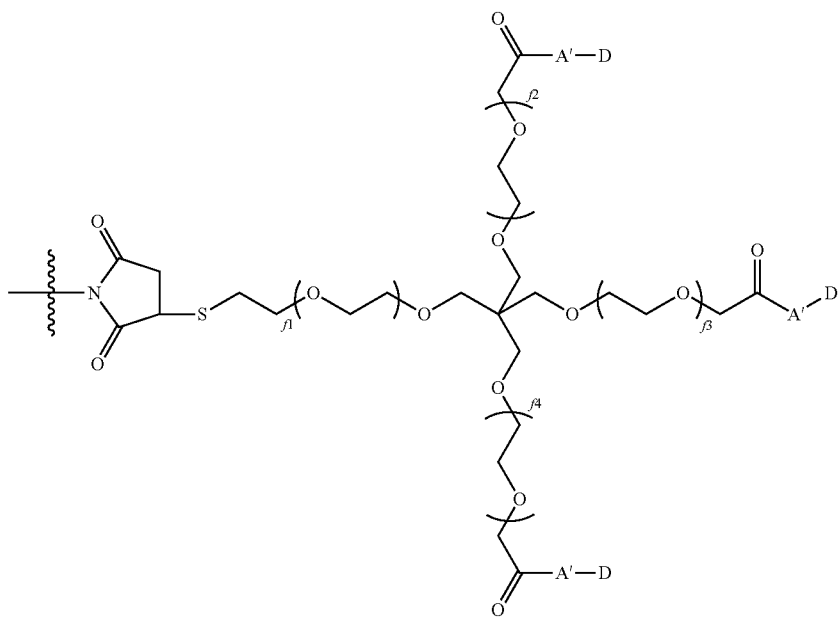

Wherein TM is a ligand unit, A' is a spacer, D is a drug, and e1 to e4 and f1 to f4 are independently selected from an integer from 1 to 240, preferably from an integer from 1 to 120, more preferably from 1 to 80, further preferably an integer from 1 to 40. The TM, A' and D have the above definitions of the invention.

In a preferred embodiment of the invention, in the above formula VIII, e1 to e4 are an equal integer.

In a preferred embodiment of the invention, in the above formula VIII, f1 to f4 are an equal integer.

In a preferred embodiment of the invention, in the above formula VIII, the TM is an anti-HER2 monoclonal antibody, preferably a recombinant anti-HER2 humanized monoclonal antibody.

In one embodiment of the invention, in the above formula VIII, the A' is a Valine residue.

In an embodiment of the invention, in the above VIII, the -A'-D has a structure of:

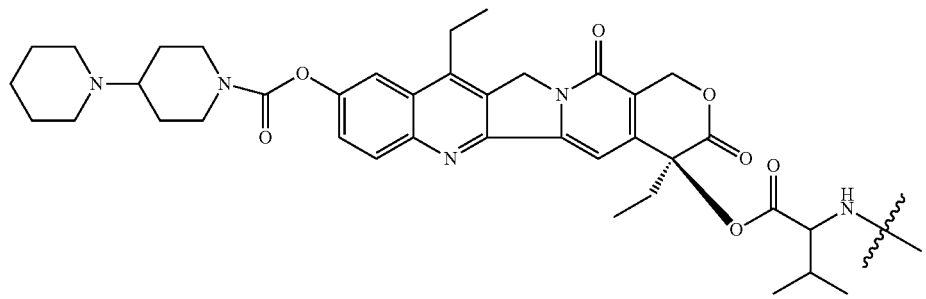 [SMILES: *NC(C(=O)O[C@]1(CC)C(=O)OCc2c1cc1n(c2=O)Cc2c-1nc1ccc(OC(=O)N3CCC(N4CCCCC4)CC3)cc1c2CC)C(C)C]

In still another embodiment of the present invention, in the above formula VIII, A' is a single bond.

In another embodiment of the invention, in the above VIII, -A'-D has a structure of:

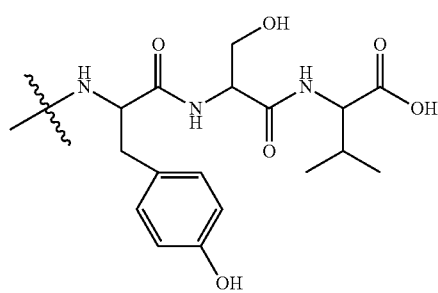 [SMILES: *NC(Cc1ccc(O)cc1)C(=O)NC(CO)C(=O)NC(C(=O)O)C(C)C]

Another aspect of the present invention provides a pharmaceutically acceptable salt of the ligand drug conjugate of the present invention, the pharmaceutically acceptable salt comprising an organic salt or an inorganic salt selected from one or more of: sodium salt, potassium salt, cesium salt, calcium salt, magnesium salt, triethylamine salt, pyridine salt, methylpyridine salt, ethanolamine salt, triethanolamine salt, dicyclohexylamine salt, N,N-dibenzylethylenediamine salt, hydrochloride, hydrobromide, sulfate, nitrate, phosphate, formate, acetate, trifluoroacetate, pantothenate, succinate, citrate, tartrate, fumarate, maleate, gluconate, glucuronate, saccharate, benzoate, lactate, methanesulfonate, ethanesulfonate, besylate, p-toluenesulfonate, argininate, aspartate, glutamate, pantothenate, and ascorbate.

Another aspect of the invention also provides a pharmaceutical composition comprising the ligand drug conjugate of the invention and a pharmaceutically acceptable carrier or excipient.

In an embodiment of the invention, the pharmaceutically acceptable composition will comprise from about 1 to about 99% by weight of the conjugate of the invention, and from 99 to 1% by weight of a suitable carrier or pharmaceutical excipient, depending on the mode of administration desired.

Preferably, the compositions comprise from about 5 to 75% by weight of a combination of the invention, the balance being a suitable carrier or pharmaceutically acceptable excipient.

More preferably, the composition comprises from about 10 to 50% by weight of a combination of the invention, the balance being a suitable carrier or pharmaceutically acceptable excipient.

In an embodiment of the present invention, the pharmaceutical composition of the present invention may further comprise a small amount of an auxiliary substance, such as a wetting agent or an emulsifier, a pH buffering agent, an antioxidant, a solubilizing agent, etc., for example, citric acid, sorbitan monolauric acid ester, a triethanolamine oleate, a butylated hydroxytoluene or the like.

Preferably, the solubilizing agent is selected from the group consisting of: L-histidine, L-histidine hydrochloride, trehalose, Tween, isosteviol, poloxamer, hydroxypropyl-β-cyclodextrin, Span, glyceryl monostearate, glyceryl distearate, polyoxyethylene castor oil, hydrogenated castor oil, polyoxyethylene hydrogenated castor oil, polyoxyethylene stearate and soybean phospholipid.

In an embodiment of the present invention, the pharmaceutical composition may be in a form of a tablet, a capsule, a pill, a granule, a powder, a suppository, an injection, a solution, a suspension, a paste, a patch, a lotion, a drop, a liniment or a spray.

In an embodiment of the invention, the conjugate of the invention may be administered in the form of a pure compound or a suitable pharmaceutical composition, and may be carried out by using any of the acceptable modes of administration or agents for similar uses.

Thus, the mode of administration employed may be selected by oral, intranasal, parenteral, topical, transdermal or rectal administration in the form of a solid, semi-solid or liquid pharmaceutical form, for example, tablets, suppositories, pills, soft and hard gelatin capsules, powders, solutions, suspensions, injections and the like, preferably is administrated in unit dosage forms suitable for simple administration of precise dosages.

The pharmaceutical composition which can be administered in a liquid form may be dissolved or dispersed in a carrier, for example, by dissolving, dispersing the conjugate of the present invention (about 0.5 to about 20%) and the optional pharmaceutical excipient in a carrier to form a solution or suspension. Examples of the carrier are water, saline, aqueous dextrose, glycerol or ethanol, etc.

Another aspect of the present invention provides a use of ligand drug conjugate, or a pharmaceutically acceptable salt thereof, and the above pharmaceutical composition in the manufacture of a medicament for preventing and/or treating a disease.

In an embodiment of the invention, the disease is cancer, a pathogenic biological infection or an autoimmune disease.

wherein the cancer may be a hematopoietic tumor, a cancer, a sarcoma, a melanoma or a glioma tumor.

wherein the pathogenic organism is selected from the group consisting of: human immunodeficiency virus (HIV), *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus* sp., *Haemophilus influenzae* type B, *Treponema pallidum*, Lyme disease spirochete, West Nile virus, *Pseudomonas aeruginosa, Mycobacterium leprae, Alcaligenes abortus*, rabies virus, influenza virus, cytomegalovirus, herpes simplex virus type I, herpes simplex virus type II, human serum parvovirus, respiratory syncytial virus, varicella-zoster virus, type B Hepatitis virus, measles virus, adenovirus, human T cell leukemia virus, Epstein-Barr virus, murine leukemia virus, mumps virus, vesicular stomatitis virus, Sindbis virus, lymphocytic choriomeningitis virus, wart virus, bluetongue virus, Sendai virus, feline leukemia virus, reovirus, poliovirus, simian virus 40, murine mammary tumor virus, dengue virus, Rubella virus, *Plasmodium falciparum, Plasmodium vivax, Toxoplasma gondii* and *Trypanosoma rangeli*;

wherein the autoimmune disease is selected from the group consisting of: immune-mediated thrombocytopenia, dermatomyositis, Sjogren's syndrome, multiple sclerosis, Sydenham's chorea, myasthenia gravis, Systemic lupus erythematosus, lupus nephritis, rheumatic fever, rheumatoid arthritis, polyglandular syndrome, bullous pemphigoid, diabetes, Schoehlein-Henoch purpura, post-streptococcal infection nephritis, nodular Erythema, Takayasu's arteritis, Addison's disease, sarcoidosis, ulcerative colitis, erythema multiforme, IgA nephropathy, nodular polyarteritis, mandatory spondylitis, Goodpasture's syndrome, thromboangiitis angiitis, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, myelophthisis, giant cell arteritis/polymyalgia, pernicious anemia, acute glomerulonephritis, fibrosing alveolitis, and juvenile diabetes.

The invention also provides a method of treating a disease comprising administering to a subject a ligand drug conjugate of the invention, or a pharmaceutically acceptable salt or pharmaceutical composition thereof.

In a specific embodiment of the invention, the ligand drug conjugate or a pharmaceutically acceptable salt or pharmaceutical composition thereof is administered in combination with one or more of the following therapeutic means: unconjugated antibody, radiolabel antibodies, drug-conjugated antibodies, toxin-conjugated antibodies, gene therapy, chemotherapy, therapeutic peptides, oligonucleotides, local radiotherapy, surgery, and interfering RNA therapy.

In an embodiment of the invention, the disease is cancer, a pathogenic biological infection or an autoimmune disease.

Wherein the cancer is a hematopoietic tumor, a cancer, a sarcoma, a melanoma or a glial tumor. Wherein the pathogenic organism is selected from the group consisting of human immunodeficiency virus (HIV), *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus* sp., *Haemophilus influenzae* type B, *Treponema pallidum*, Lyme disease spirochete, West Nile virus, *Pseudomonas aeruginosa, Mycobacterium leprae, Alcaligenes abortus*, rabies virus, influenza virus, cytomegalovirus, herpes simplex virus type I, herpes simplex virus type II, human serum parvovirus, respiratory syncytial virus, varicella-zoster virus, type B Hepatitis virus, measles virus, adenovirus, human T cell leukemia virus, Epstein-Barr virus, murine leukemia virus, mumps virus, vesicular stomatitis virus, Sindbis virus, lymphocytic choriomeningitis virus, wart virus, bluetongue virus, Sendai virus, feline leukemia virus, reovirus, poliovirus, simian virus 40, murine mammary tumor virus, dengue virus, Rubella virus, *Plasmodium falciparum, Plasmodium vivax, Toxoplasma gondii* and *Trypanosoma rangeli*;

wherein the autoimmune disease is selected from the group consisting of immune-mediated thrombocytopenia, dermatomyositis, Sjogren's syndrome, multiple sclerosis, Sydenham's chorea, myasthenia gravis, Systemic lupus erythematosus, lupus nephritis, rheumatic fever, rheumatoid arthritis, polyglandular syndrome, bullous pemphigoid, diabetes, Schoehlein-Henoch purpura, post-streptococcal infection nephritis, nodular Erythema, Takayasu's arteritis, Addison's disease, sarcoidosis, ulcerative colitis, erythema multiforme, IgA nephropathy, nodular polyarteritis, mandatory spondylitis, Goodpasture's syndrome, thromboangiitis angiitis, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, myelophthisis, giant cell arteritis/polymyalgia, pernicious anemia, acute glomerulonephritis, fibrosing alveolitis, and juvenile diabetes.

Another aspect of the present invention provides a method for preparing the above-mentioned ligand drug conjugate, and the synthesis steps of the preparation method are schematically as follows:

(1) PEG1+modifying group=[PEG-1],
(2) [PEG-1]+ligand unit=ligand unit–[PEG-1] (Compound A),
(3) PEG2+modifying group=[PEG-2],
(4) Drug+[PEG-2]=[PEG-2]–drug (Compound B),
(5) Compound A+Compound B=ligand drug conjugate; or,
(1) PEG1+modifying group=[PEG-1],
(2) PEG2+modifying group=[PEG-2],
(3) Drug+[PEG-2]=[PEG-2]–drug (Compound B),
(4) [PEG-1]+Compound B=[PEG-1]–[PEG-2]–drug (Compound C),
(5) Ligand unit+Compound C=ligand drug conjugate; or,
(1) PEG1+modifying group=[PEG-1],
(2) PEG2+modifying group=[PEG-2],
(3) [PEG-1]+[PEG-2]=[PEG-1]–[PEG-2] (Compound D),
(4) Compound D+drug=[PEG-1]-[PEG-2]–drug (Compound C),
(5) Ligand unit+compound C=ligand drug conjugate.

In an embodiment of the invention, the [PEG-1] is a double- or multi-terminal modified polyethylene glycol residue, with at least one end comprising a reactive end group Z1 attached to a ligand unit, and at least one end comprising a reactive end group Z2 attached to PEG2;

The reactive end group Z1 is selected from the group consisting of: succinimide group, mercapto group, carboxyl group, propionic acid group, aldehyde group, acrylic group, glutaric acid group, maleimide group, N-hydroxy-succinimide group, N-hydroxy-glutarimide, succinimide carbonate, succinimide acetate, succinimide propionate, succinimide succinate, imidic acid ester group, p-nitrophenyl carbonate group, melamine group, o-dithiopyridyl group, thioester group, hydrazide group, isocyanate group, isothiocyanate group and vinyl sulfone group;

The reactive end group Z2 is selected from the group consisting of: an ethynyl group, an azide group, a sulfhydrylgroup, a sulfhydryl-reactive group capable of reacting with a sulfhydryl group to form a thioether bond or a disulfide bond, including but not limited to: maleimide group, glutaric acid group, vinyl sulfone group, haloacetamide group, pyridyl disulfide group, thiosulfonate group, ethyleneimine group, aziridine group, aminosulfonyl group;

The [PGE-2] is a double-end or multi-end modified polyethylene glycol residue, with at least one end comprising a reactive end group Z3 reactive with the reactive end group Z2, and at least one end comprising a reactive end group Z4;

The reactive end group Z3 is selected from the group consisting of: an ethynyl group, an azide group, a fluorenyl group, a fluorenyl-reactive group capable of reacting with a fluorenyl group to form a thioether bond or a disulfide bond, including but not limited to: maleimide group, glutaric acid group, vinyl sulfone group, haloacetamide group, pyridyl disulfide group, thiosulfonate group, ethyleneimine group, aziridine group, aminosulfonyl group;

The reactive end group Z4 is a carboxyl group, a hydroxyl group or a carbonyl group.

In the embodiment of the present invention, a linking group can be further included between the reactive end group Z1 and Z2, Z3, Z4 and the polyethylene glycol residue, and the linking group includes but is not limited to: —$(CH_2)_i$—, —$(CH_2)_i$NH—, —$(CH_2)_i$OCOO—, —$(CH_2)_i$OCONH—, —$(CH_2)_i$NHCONH—, —$(CH_2)_i$NHCO—, —OC$(CH_2)_i$COO—, —$(CH_2)_i$COO— and —$(CH_2)_i$CONH—, or the combination thereof, and i is an integer from 0- to 10; preferably, i is 0, 1 or 2.

Compared with the prior art, the present invention has the following advantageous effects:

The ligand drug conjugates provided by the present invention employ a PEG linker to couple a drug and a ligand unit, wherein, in a preferred embodiment of the present invention, a plurality of drug molecules are linked by branching or multi-arm PEG to enhance drug loading. At the same time, due to the hydrophilicity of PEG, while ensuring high drug load, it can also ensure that its pharmacokinetic characteristics are close to those of low-load antibody-conjugated drugs.

The ligand drug conjugates provided by the present invention are characterized by high loading, high drug efficiency, low toxicity, and low risk. In a preferred embodiment, they are particularly useful for attaching drug molecules with low toxicity, thereby expanding the therapeutic window.

Further, the antibody-conjugated drug molecule provided by the invention can allow the antibody-coupled drug to carry a large number of low-toxic drug molecules due to its multi-drug and high-load characteristics, and can achieve therapeutic effect independent of the drug-targeting effect and the highly toxic drug. Thus it has a wider range of antibodies available.

Ab: naked anti-antibody (recombinant anti-HER2 humanized monoclonal antibody); APEGA-8: antibody drug conjugate (single arm+single arm, prepared in Example 6); APEGA-9: antibody drug conjugate (four arm+single arm, prepared in Example 7; APEGA-10: antibody drug conjugate (four arms+four arms, prepared in Example 8).

Figure 2:
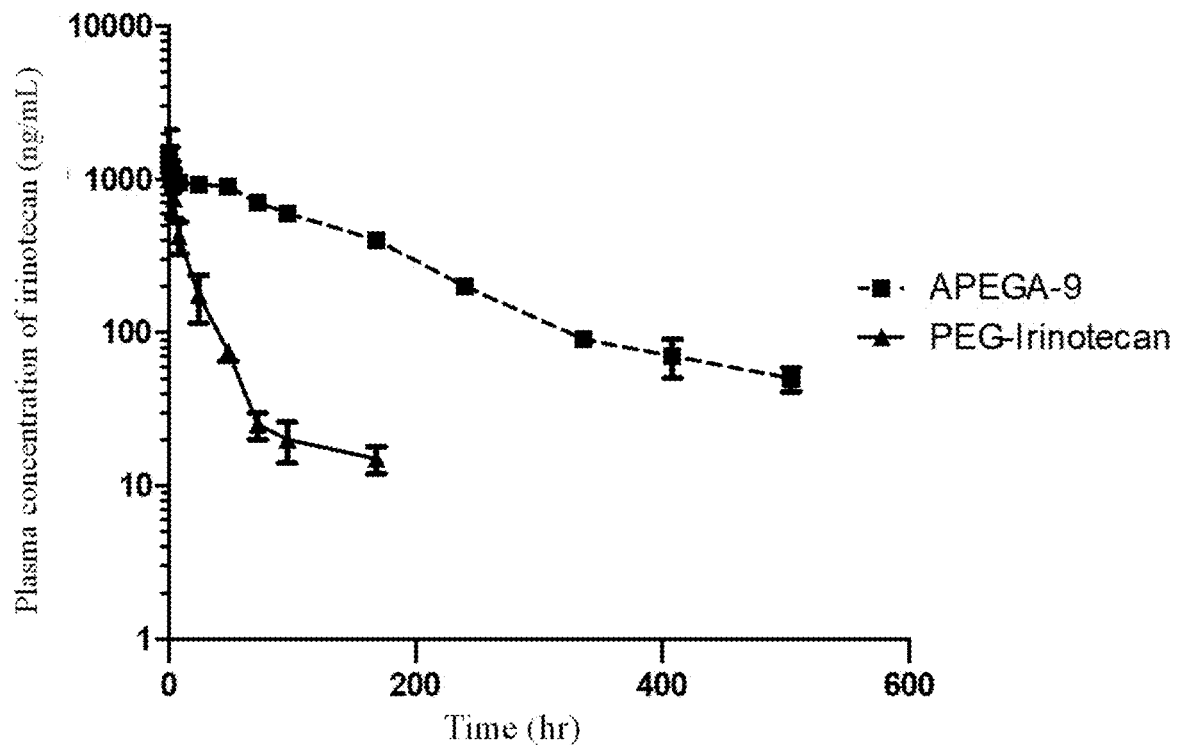

FIG. 2 is a graph of rat plasma drug-time (Irinotecan concentration, ng/mL Vs time, hr). The intravenous injection doses of PEG-Irinotecan and APEGA-9 were both 4.2 mg/kg in term of Irinotecan.

APEGA-9: antibody drug conjugate (four arms+single arm, prepared in Example 7); PEG-Irinotecan (PEG5K-PEG3.5K-Irinotecan): PEG drug conjugate (four arms+singlearm, prepared in Example 5).

Figure 3:
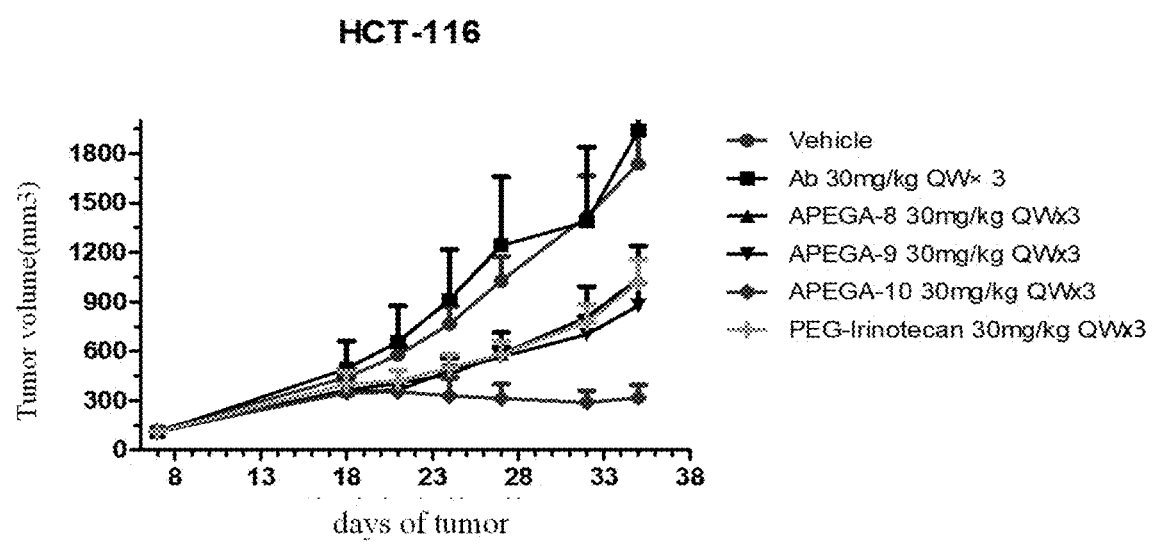

FIG. 3 is a graph showing the mean tumor volume in the colorectal cancer model (HCT-116) corresponding to the days after tumor transplantation, the dose of Ab and the antibody conjugate 30 mg/kg, and the PEG-Drug administered 30 mg in term of Irinotecan.

Ab: naked anti-antibody; APEGA-8: antibody drug conjugate (single arm+single arm, prepared in Example 6); APEGA-9: antibody drug conjugate (four arms+single arm, prepared in Example 7); APEGA-10: antibody drug conjugate (four arms+four arms, prepared in Example 8); PEG-Irinotecan (PEG5K-PEG3.5K-Irinotecan): PEG drug conjugate (four arms+single arm, prepared in Example 5).

DETAILED DESCRIPTION OF THE INVENTION

Unless otherwise stated, the terms hereinafter have the following meanings.

The term "antibody" as used herein is used in its broadest sense and specifically covers monoclonal antibodies, polyclonal antibodies, dimers, multimers, multispecific antibodies (eg, bispecific antibodies) and antibody fragments, as long as they show desired biological activity (Miller et al. (2003) Jour. of Immunology, 170: 4854-4861). The antibody can be murine, human, humanized, chimeric, or derived from other species. Antibodies are proteins produced by the immune system that recognize and bind specific antigens (Janeway, C. et al. (2001) ImmunoBiology, 5th Ed., Garland Publishing, New York). Target antigens generally have a large number of binding sites, also referred to as epitopes, which are recognized by the CDRs of a variety of antibodies. Each antibody that specifically binds to a different epitope has a different structure. Thus, an antigen can correspond to more than one antibody.

Antibodies include full length immunoglobulin molecules or immunologically active portions of full length immunoglobulin molecules, i.e, molecules containing antigens or portions thereof that specifically bind to a target of interest. Such targets includes, but not limited to cancer cells or cells that produce autoimmune antibodies associated with immune diseases. In particular, the antibodies of the invention are reactive against cancer cells, malignant cells, infectious organisms or antigens associated with autoimmune diseases or epitopes thereof. The immunoglobulins disclosed herein can have any type of immunoglobulin molecule (for example, IgG, IgE, IgM, IgD, and IgA), classes (for example, IgG1, IgG2, IgG3, IgG4, IgA, IgA2) or subclasses. The immunoglobulins can be derived from any species. However, in one aspect, the immunoglobulin is derived from a human, a mouse or a rabbit.

The term "antibody fragment" herein encompasses a portion of a full length antibody, typically its antigen binding or variable region. Examples of antibody fragments include: Fab, Fab', F(ab')2 and Fv fragments; diabodies; linear antibodies; minibodies (Olafsen et al. (2004) Protein Eng. Design & Sel. 17(4): 315-323); fragments prepared from Fab expression libraries; anti-idiotype (anti-Id) antibodies; CDRs (complementarity determining regions); and any of the above epitope-binding fragments immunologically specifically binding to cancer cell antigens, viral antigens or microbial antigen; a mono-chain antibody molecule; and a multispecific antibody formed from the antibody fragment.

The term "monoclonal antibody" as used herein refers to an antibody obtained from a substantially homogeneous population of antibodies, i.e., the antibodies contained in the population are identical except for naturally occurring possible mutations that may be present in minor amounts. Monoclonal antibodies are highly specific antibodies that target a single antigenic site. Moreover, in contrast to polyclonal antibody preparations which typically include different antibodies that target different antigenic determinants (epitopes), each monoclonal antibody only targets a single determinant on the antigen. In addition to their specificity, monoclonal antibodies have the advantage that they can be synthesized in a manner that is not contaminated by other antibodies. The modifier "monoclonal" denotes the property of an antibody obtained from a substantially homogeneous population of antibodies and is not to be construed as producing the antibody by any particular method. For example, a monoclonal antibody used in the present invention can be prepared by the hybridoma method first described by Kohler et al. (1975) Nature 256:495 or can be prepared by recombinant DNA methods (for example: U.S. Pat. Nos. 4,816,567; 5,807,715). For example, monoclonal antibodies can be separated from phage antibody libraries by the technique described by Clackson et al. (1991) Nature, 352: 626-628; Marks et al. (1991) J. Mol. Biol., 222: 581-597.

A "monoclonal antibody" herein specifically includes a "chimeric" antibody wherein a portion of the heavy and/or light chain is identical or homologous to a corresponding sequence of antibody derived from a particular species or belonging to a particular antibody type or subtype, and the remainder of the strand is identical or homologous to the corresponding sequence in an antibody derived from another species or belonging to another antibody type or subtype. The fragments of the chimeric antibodies are also included herein so long as they exhibit the desired biological activity (U.S. Pat. No. 4,816,567; and Morrison et al. (1984) Proc. Natl. Acad. Sci. USA, 81: 6851-6855). Chimeric antibodies of interest herein include "primatized" antibodies comprising antigen-binding sequences of variable region derived from non-human primates and human constant region sequences.

The term "intact antibody" herein comprises antibodies of the VL and VH domains as well as the light chain constant domain (CL) and the heavy chain constant domains CH1, CH2 and CH3. The constant domain can be a native sequence constant domain (for example, a human native sequence constant domain) or an amino acid sequence variant thereof. An intact antibody may have one or more "effector functions", meaning those biological activities due to the Fc constant region of the antibody (the native sequence Fc region or the amino acid sequence variant Fc region). Examples of antibody effector functions include Clq binding; complement dependent cytotoxicity; Fc receptor binding; antibody-dependent cell mediated cytotoxicity (ADCC); endocytosis; and cell surface receptors, such as B cell receptors and down-regulation of body and BCR.

Depending on the amino acid sequence of its heavy chain constant domain, intact antibodies can be assigned to five major classes of intact immunoglobulin antibodies: IgA, IgD, IgE, IgG, and IgM, and several of them can be further divided into "subclasses" (subtypes) such as IgG1, IgG2, IgG3, IgG4, IgA1 and IgA2. The heavy chain constant domains corresponding to different antibody classes are referred to as $\alpha$, $\delta$, $\epsilon$, $\gamma$, and $\mu$, respectively. The subunit structures and three-dimensional configurations of different classes of immunoglobulins are well known. Type Ig includes hinge-modified or hinge-free (Roux et al. (1998) J. Immunol. 161: 4083-4090; Lund et al. (2000) Eur. J. Biochem. 267: 7246-7256; US 2005/0048572; US 2004/0229310).

The term "parent antibody" as used herein is an antibody in which one or more amino acid residues in the amino acid sequence is replaced with one or more cysteine residues. The parent antibody can include a native or wild type sequence. The parent antibody may comprise a native or wild type sequence. The parent antibody may have pre-existing amino acid sequence modifications (such as additions, deletions, and/or substitutions) relative to other native, wild-type or modified forms of the antibody. The parent antibody can be directed against a target antigen of interest, such as a biologically important polypeptide. Antibodies directed against non-polypeptide antigens, such as tumor-associated glycolipid antigens; see U.S. Pat. No. 5,091,178, are also of interest. Exemplary parent antibodies include selective antibodies that have affinity for cell surface and transmembrane receptors and tumor associated antigens (TAA).

The term "antigen bound to an antibody" as used herein includes, but is not limited to, HER-2/neu, carbonic anhydrase IX, B7, CCCL19, CCCL21, CSAp, BrE3, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM-6, alpha-fetoprotein (AFP), VEGF, ED-B fibronectin, EGP-1, EGP-2, EGF receptor (ErbB1), ErbB2, ErbB3, factor H, FHL-1, Flt-3, folate receptor, Ga733, GROB, HMGB-1, hypoxia-inducible factor (HIF), HM1 0.24, insulin-like growth factor (ILGF), IFN-γ, IFN-α, IFN-J3, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, ganglioside, HCG, HLA-DR, CD66a-d, MAGE, mCRP, MCP-1, MIP-1A, MIP-1B, macrophage migration inhibitory factor (M IF), MUC1, MUC2, MUC3, MUC4, MUC5, placental growth factor (PIGF), PSA, PSMA, PSMA dimer, PAM4 antigen, NCA-95, NCA-90, A3, A33, Ep-CAM, KS-1. Le(y), mesothelin, S100, tenascin, TAC, Tn antigen, Thomas-Friedenreich antigen, tumor necrosis antigen, tumor angiogenic antigen, TNF-α, TRAIL receptor (R1 and R2), VEGFR, RANTES, T101, cancer stem cell antigen, complement factor C3, C3a, C3b, C5a, C5 and oncogene products, etc.

EXAMPLE

The various embodiments of the invention are illustrated by the following examples, but are not intended to limit the invention.

The irinotecan used in the Examples was purchased from Shanghai Longxiang Biomedical Development Co, Ltd, 4-dimethylaminopyridine (DMAP) and 1-hydroxybenzotriazole (HOBT) from Shanghai Covalent Chemical Technology Co, Ltd. The polyethylene glycol derivative was purchased from Beijing Keykai Technology Co, Ltd, and other reagents were purchased from Sinopharm Group.

[PEG-1] Synthesis Example

Example 1: Synthesis of Four-Arm Polyethylene Glycol Maleimide-Succinimidyl Acetate (V-3)

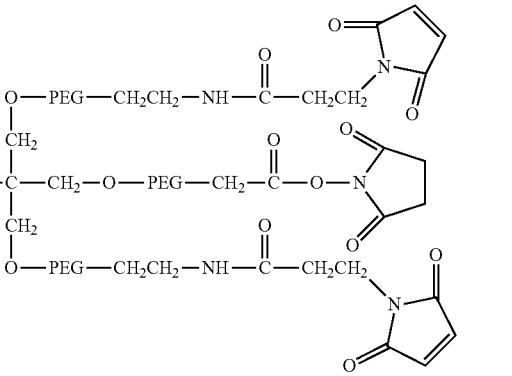

(MAL)3-4ARMPEG5K-NHS

Procedure:

Four-arm polyethylene glycol maleimide-succinimidyl acetate (V-3) was prepared by following the procedure of Examples 1-9 of Patent Application CN201610398765.4.

NMR (DMSO) δ: 2.32

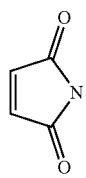

(t, 6H, 2.82

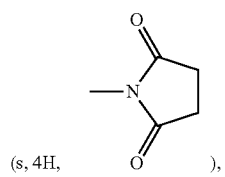

(s, 4H, ), 3.15 (q, 6H, $CH_2CH_2NH$), 4.60 (s, 2H, $CH_2COO$), 6.99 (s, 6H, 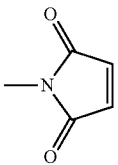 ).

[PEG-2] Synthesis Example

Example 2: Preparation of SH-PEG-(CONHI)$_3$(5K)(T2-4)

$HS\text{-}PEG\text{-}(CONHI)_3$   T2-4

SH-PEG-(CONHI)$_3$(5K)(T2-4) was prepared by following the procedure of Examples 36-39 of the patent application CN201610398765.4.

$^1$H NMR (300 MHz, DMSO-d$_6$) δ: 8.09 (d, 3H), 7.92 (d, 3H), 7.67 (m, 3H), 7.43 (m, 3H), 7.12 (s, 3H), 5.37 (s, 6H), 5.03 (s, 6H), 4.35-4.22 (m, 9H), 4.19 (s, 6H), 4.07 (s, 6H), 3.13 (s, 9H), 2.86-2.67 (m, 9H)), 2.35 (m, 4H), 2.28 (d, 3H), 2.09-1.98 (m, 6H), 1.76-1.53 (m, 30H), 1.31 (s, 9H), 0.91 (m, 9H).

Example 3: Preparation of SH-PEG-CONHI (3.5K) (T5-6)

$HS\text{-}PEG\text{-}CONHI$   T5-6

SH-PEG-CONHI (3.5K) (T5-6) was prepared by following the procedure of Examples 46-51 of the patent application CN201610398765.4.

$^1$H NMR (300 MHz, DMSO-d$_6$) δ: 8.09 (d, 1H), 7.92 (d, 1H), 7.67 (m, 1H), 7.43 (m, 1H), 7.12 (s, 1H), 5.37 (s, 2H), 5.03 (s, 2H), 4.35-4.22 (m, 3H), 4.19 (s, 2H), 4.07 (s, 6H), 3.81-3.49 (m, 150H), 3.13 (s, 3H)), 2.86-2.67 (m, 3H), 2.35 (m, 4H), 2.28 (d, 1H), 2.09-1.98 (m, 2H), 1.76-1.53 (m, 10H), 1.31 (s, 9H), 0.91 (m, 9H).

Example 4: Preparation of SH-4ARMPEG5K-(CONH-YSV)3

(1) Preparation of HCl.Tyr-Ser-Val-OMe 8.4 g (17.5 mmol) of Boc-Tyr-Ser-Val-OMe (prepared according to CN100519576C) was added portionwise to the cooled 4M HCl/ethyl acetate. After the addition, the mixture was stirred at the same temperature for 2 hours, and the TLC was monitored until the disappearance of the starting material; then filtrated and the precipitate was washed with ethyl acetate (50 mL*3) and dry diethyl ether (50 mL*3), and dried. 5.7 g product was obtained, which was used directly for the next reaction.

(2) Preparation of Py-S-S-PEG-(CONH-Tyr-Ser-Val-OMe)$_3$(5K)

2.5 g (0.5 mmol) of Py-SS-PEG-(COOH)$_3$ and 2.3 g (4.5 mmol) of tyroservatide methyl ester hydrochloride (HCl-.Tyr-Ser-Val-OMe), 932 mg (7 mmol) of HOBt were placed into the reaction flask, dissolved in dichloromethane, then added with 1.8 mL (10.5 mmol) of diisopropylethylamine, homogenized by stirring, added with 1.34 g (7 mmol) of EDCI, after that, stirred at room temperature overnight, and concentrated to dryness. The residue was crystallized with isopropanol, filtered and dried to give a white solid.

$^1$H NMR (300 MHz, DMSO-d$_6$) δ: 8.57 (s, 1H), 8.23 (s, 3H), 8.17 (s, 3H), 8.12 (s, 3H), 7.72 (m, 1H), 7.47 (d, 1H), 7.26 (d, 1H), 7.12 (d, 6H), 6.98 (d, 6H), 5.03 (m, 3H), 4.88 (m, 3H), 4.53 (m, 3H), 4.19 (d, 6H), 3.87 (s, 9H), 3.18 (m, 9H), 1.12 (d, 18H).

(3) Preparation of Py-S-S-PEG-(CONH-Tyr-Ser-Val-OH)$_3$(5K)

2.1 g (0.4 mmol) of Py-SS-PEG-(CONH-Tyr-Ser-Val-OMe)$_3$ was dissolved in 20 mL of methanol, cooled to 0° C., and slowly added with 2 mL of 2M NaOH aqueous solution, and stirred at the same temperature after the completion of the dropwise addition. After 6 hours, TLC was monitored until the disappearance of the starting material. The reaction solution was adjusted to neutral with KHSO$_4$ aqueous solution. The mixture was concentrated under reduced pressure to remove methanol, then adjusted to pH 1-2 with KHSO$_4$ aqueous solution, extracted with dichloromethane. The organic layers were combined, washed to become neutral, dried, and filtered. The filtrate was evaporated to dryness, and the residue was crystallised by using isopropyl alcohol, filtered, and dried to give 1.8 g product as a white solid.

$^1$H NMR (300 MHz, DMSO-d6) δ: 8.57 (s, 1H), 8.23 (s, 3H), 8.17 (s, 3H), 8.12 (s, 3H), 7.72 (m, 1H), 7.47 (d, 1H), 7.26 (d, 1H), 7.12 (d, 6H), 6.98 (d, 6H), 5.03 (m, 3H), 4.88 (m, 3H), 4.53 (m, 3H), 4.19 (d, 6H), 3.18 (m, 9H), 1.12 (d, 18H).

(4) Preparation of SH-PEG-(CONH-Tyr-Ser-Val-OH)$_3$ (5K)

1.5 g (0.3 mmol) of Py-SS-PEG-(CONH-Tyr-Ser-Val-OH)$_3$ as the raw material was taken, dissolved in dichloromethane, added with DTT and triethylamine, stirred at room temperature overnight. The reaction solution is concentrated to dry, the residue was crystallised with isopropanol, filtered, and dried to give 1.2 g product as a white solid.

$^1$H NMR (300 MHz, DMSO-d6) δ: 8.23 (s, 3H), 8.17 (s, 3H), 8.12 (s, 3H), 7.12 (d, 6H), 6.98 (d, 6H), 5.03 (m, 3H), 4.88 (m, 3H), 4.53 (m, 3H), 4.19 (d, 6H), 3.18 (m, 9H), 1.12 (d, 18H).

COUPLING—EXAMPLES

Example 5: Preparation of [PEG-1A]-[PEG-2A]-Drug

[PEG-1A]-[PEG-2A]-Drug was prepared from(MAL)3-4ARMPEG5K-NHS (V-3, prepared in Example 1) and SH-PEG3.5K-CONHI (T5-6, Example 3)), which has a structural formula of:

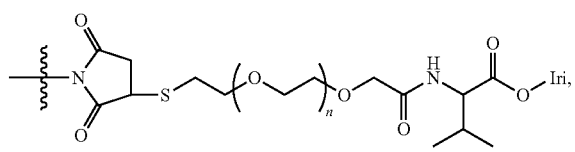

wherein,
Y is

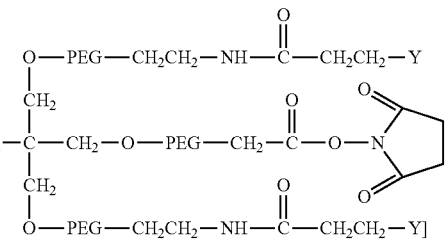

Iri is

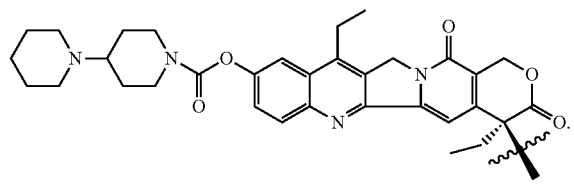 [SMILES: CCc1c2c(nc3ccc(OC(=O)N4CCC(N5CCCCC5)CC4)cc13)-c1cc3c(c(=O)n1C2)COC(=O)[C@]3(C)CC]

Step 1, feed at a molar ratio of V-3:T5-6=1:3.6 (a mass ratio of about 1:2.8), the total volume of 14 mL;

The V-3 solution (125 mg/mL) was freshly prepared using 1 mM diluted hydrochloric acid, and 3.44 mL (430 mg) was weighed and rapidly added to 10.64 mL of equilibration buffer (PEG1 concentration: 30.7 mg/mL). A T5-6 solution (172 mg/mL) was freshly prepared using 1 mM diluted hydrochloric acid, and 7 mL (1204 mg) was weighed and rapidly added to the above V-3 solution to be used as PEG5K-PEG3.5K-Irinotecan reaction group. (T5-6 final concentration 43 mg/mL, V-3 final concentration 15.4 mg/mL).

Step 2, remove free PEG-Irinotecan by ultrafiltration (1) Membrane ultrafiltration, molecular weight cutoff 50 KD;

(2) The rotation speed is 100 rpm, and the concentration multiple of each time is recorded;

(3) The filtrate was quantified by UV carried out until the free PEG-Irinotecan did not interfere with the quantification, and the solution was replaced with 50 mM PB, pH 6.0, 97 mM NaCl solution, and the Irinotecan concentration was adjusted to 3.0 mg/mL. A further filtration and sterilization was carried out to give a conjugate.

Example 6: Preparation of a Ligand Drug Conjugate (APEGA-8)

(TM-[PEG-1A]-[PEG-2A]-Drug) was prepared from MAL-PEG6-NHS (purchased from Pomeranian), SH-PEG3.5K-CONHI (T5-6, prepared in Example 3) and recombinant anti-HER2 humanized monoclonal antibody (TM), which has a structural formula of:

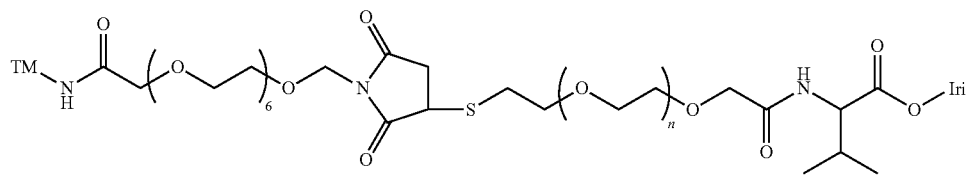

wherein,
Iri is

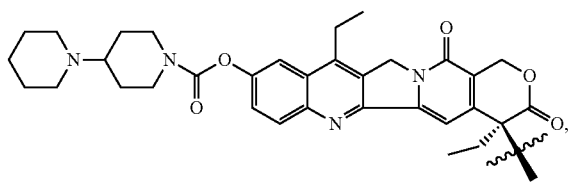 [SMILES: CCc1c2c(nc3ccc(OC(=O)N4CCC(N5CCCCC5)CC4)cc13)-c1cc3c(c(=O)n1C2)COC(=O)[C@]3(C)CC]

TM is a recombinant anti-HER2 humanized monoclonal antibody.

Step 1, the preparation of one-step coupling product (PEG1-antibody coupling reactant)

Feed at a molar ratio of TM:MAL-PEG6-NHS=1:120 (a mass ratio of about 1:0.48). 86 mg/mL MAL-PEG6-NHS solution was prepared in DMSO, and 11.2 μL was quickly added to the antibody coupling buffer system (50 mM sodium phosphate pH 6.0, 50 mM sodium chloride, 1 mM EDTA) (80.6 μL 24.8 mg/mL antibody. In 308 μL of coupling buffer). The mixture was gently shaken at room temperature, react for 2 hours to obtain a one-step coupling product; the reaction was stopped at −20° C. to terminate the reaction.

Step 2, solution replacement

The one-step coupled product was replaced by ultrafiltration to 50 mM sodium phosphate, pH 6.0.

Step 3, two-step coupling

Feed at a molar ratio of the PEG1-antibody coupling reactant:T5-6=1:1.

42 mg/mL of T5-6 solution was prepared by using 1 mM HCl, and 40 μL was quickly added to the PEG1-antibody coupling reaction solution (80 μL), and the mixture was gently shaken at room temperature, react for 2 hours; and stored at −20° C. to terminate the reaction. The free T5-6 molecule was removed by ultrafiltration and the solution was replaced with 50 mM PB, pH 6.0, 97 mM NaCl solution. A further filtration and sterilization was carried out to give a conjugate.

Example 7: Preparation of a Ligand Drug Conjugate (APEGA-9)

(TM-[PEG-1A]-[PEG-2A]-Drug) was prepared from (MAL) 3-4ARMPEG5K-NHS (V-3, prepared in Example 1), SH-PEG3.5K-CONHI (T5-6, prepared in Example 3), recombinant anti-HER2 Humanized Monoclonal Antibody (TM), which has a structural formula of:

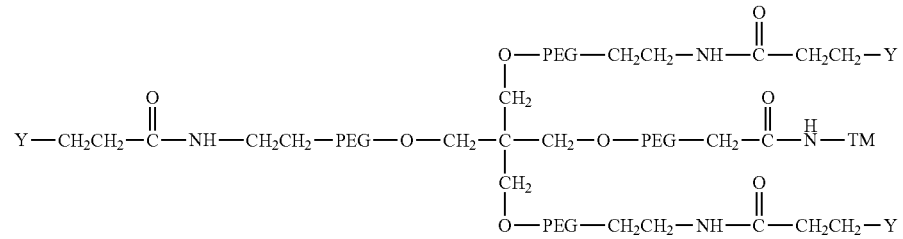

wherein,

Y is

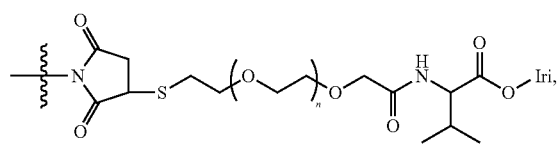

Iri is

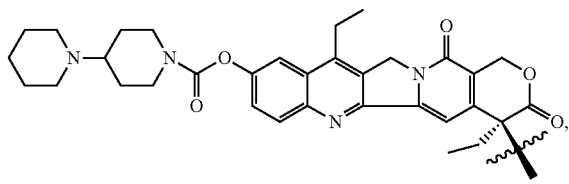 [SMILES: CCc1c2c(nc3ccc(OC(=O)N4CCC(N5CCCCC5)CC4)cc13)-c1cc3c(c(=O)n1C2)COC(=O)[C@]3(C)CC]

TM is a recombinant anti-HER2 humanized monoclonal antibody.

Step 1, the preparation of one-step coupling product (PEG1-antibody coupling reactant)

Feed at a molar ratio of antibody:V-3=1:60 (a mass ratio of about 1:2). 358 mg/mL V-3 solution was prepared in DMSO, and 11.2 μL was quickly added to the antibody coupling buffer system (50 mM sodium phosphate pH 8.0, 50 mM sodium chloride, 1 mM EDTA) (80.6 μL 24.8 mg/mL antibody in 308 μL Coupling buffer), gently shake at room temperature, react for 2 hours to obtain a one-step coupling product; store at −20° C. to terminate the reaction.

Step 2, solution replacement

The one-step coupled product was replaced by ultrafiltration to 50 mM sodium phosphate, pH 6.0.

Step 3, two-step coupling

Feed at a molar ratio of PEG1-antibody coupling reactant: T5-6=1:1. 14 mg/mL of T5-6 solution was prepared by using 1 mM HCl, and 40 μL was quickly added to the PEG1-antibody coupling reaction solution (80 μL), and the mixture was gently shaken at room temperature, react for 2 hours; and stored at −20° C. to terminate the reaction. The free T5-6 molecule was removed by ultrafiltration and the solution was replaced with 50 mM PB, pH 6.0, 97 mM NaCl solution. A further filtration and sterilization was carried out to give a conjugate.

Example 8: Preparation of Antibody Drug Conjugate (APEGA-10)

(TM-[PEG-1A]-[PEG-2A]-Drug), was prepared from (MAL) 3-4ARMPEG5K-NHS (V-3, prepared in Example 1), SH-4ARMPEG5K-(CONHI)3 (T2-4, prepared in Example 2), and recombinant anti-HER2 humanized monoclonal antibody (TM). The preparation method steps 1 and 2 refer to Example 47. It has a structural formula of:

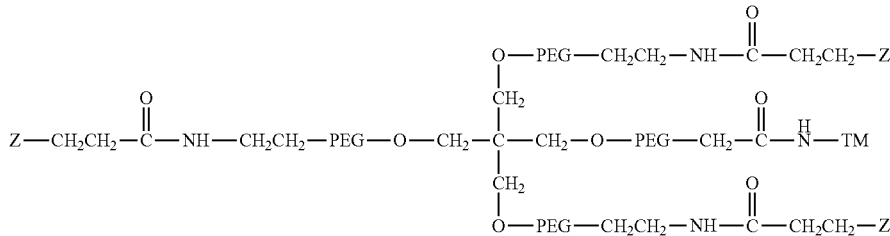

wherein
Z is

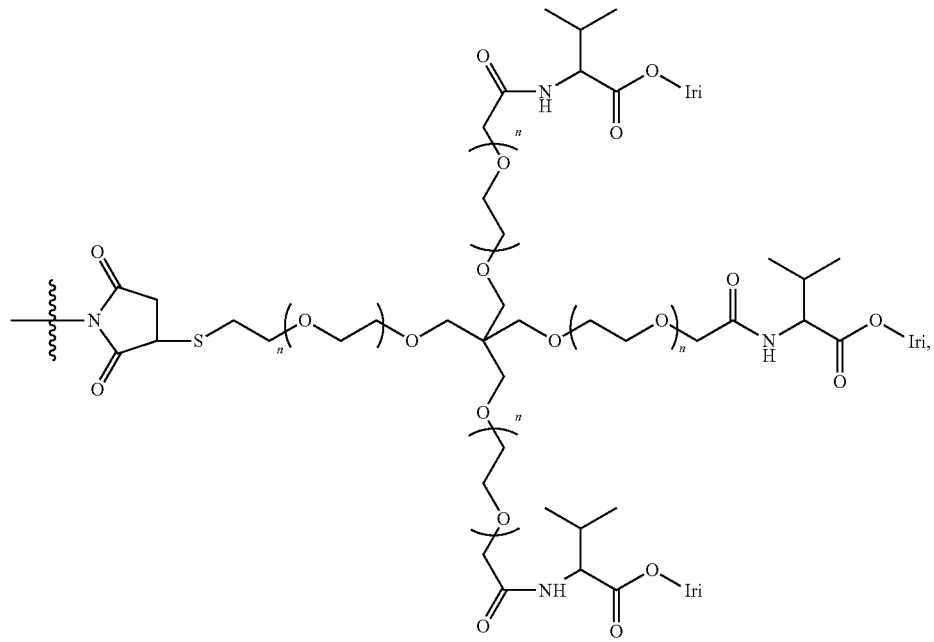

Iri is

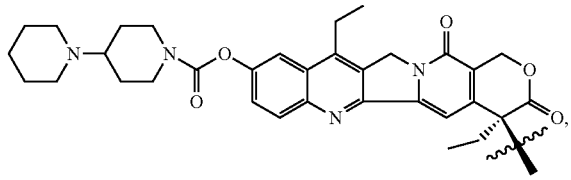 [SMILES: CCc1c2c(nc3ccc(OC(=O)N4CCC(N5CCCCC5)CC4)cc13)-c1cc3c(c(=O)n1C2)COC(=O)[C@]3(C)CC]

TM is a recombinant anti-HER2 humanized monoclonal antibody.

Step 3, two-step coupling

Feed at a molar ratio of PEG1-antibody coupling reactant: T2-4=1:1. 20 mg/mL of T2-4 solution was prepared by using 1 mM HCl, and 40 μL was quickly added to the PEG1-antibody coupling reaction solution (80 μL), and the mixture was gently shaken at room temperature for 2 hours; and stored at −20° C. to terminate the reaction. The free T2-4 molecule was removed by ultrafiltration and the solution was replaced with 50 mM PB, pH 6.0, 97 mM NaCl solution. A further filtration and sterilization was carried out to give a conjugate.

Example 9: Determination of Antibody Drug Conjugate Antibody Content in Examples 6, 7, and 8

Method: UV/Vis Method

In formula (1), the sum of the absorbances of the drug and the antibody at 280 nm constitutes the total absorbance ($A_{280}$):

$$A_{280} = (\varepsilon_{drug}^{280} C_{drug} + \varepsilon_{mAb}^{280} C_{mAb})l \quad (1)$$

wherein $\varepsilon_{drug}^{280}$ is the extinction coefficient of the drug at 280 nm; $C_{drug}$ is the drug concentration (mg/mL); E bis the extinction coefficient of the antibody at 280 nm; $C_{mAb}$ is the concentration of the antibody.

Equation (2) is the parallel equation for the total absorbance of the drug at the maximum absorption λ(D):

$$A_{\lambda(D)} = (\varepsilon_{drug}^{\lambda(D)} C_{drug} + \varepsilon_{mAb}^{\lambda(D)} C_{mAb})l \quad (2)$$

wherein $\varepsilon_{drug}^{\lambda(D)}$ is the extinction coefficient of the drug at λ(D)nm; $C_{drug}$ is the drug concentration (mg/mL); $\varepsilon_{mAb}^{\lambda(D)}$ is the extinction coefficient of the antibody at λ(D)nm; $C_{mAb}$ is the concentration of the antibody (mg/mL).

The concentration of antibody and drug can be calculated separately by two equations (1) and (2).

$$C_{mAb} = (A_{280} \varepsilon_{drug}^{\lambda(D)} - A_{\lambda(D)} \varepsilon_{drug}^{280}) / [(\varepsilon_{mAb}^{280} \varepsilon_{drug}^{\lambda(D)} - \varepsilon_{mAb}^{\lambda(D)} \varepsilon_{drug}^{280})l] \quad (3)$$

$$C_{drug} = (A_{280} \varepsilon_{mAb}^{\lambda(D)} - A_{\lambda(D)} \varepsilon_{mAb}^{280}) / [(\varepsilon_{drug}^{280} \varepsilon_{mAb}^{\lambda(D)} - \varepsilon_{drug}^{\lambda(D)} \varepsilon_{mAb}^{280})l] \quad (4)$$

The average drug antibody coupling ratio (DAR) calculated by dividing $$\frac{C_{drug}}{Mr_{drug}} \text{ by } \frac{C_{mAb}}{Mr_{mAb}}$$

is expressed as the number of moles of drug divided by the number of moles of antibody:

$$DAR = \frac{C_{drug} \times Mr_{mAb}}{C_{mAb} \times Mr_{drug}} \quad (5)$$

The result is shown in Table 1:

TABLE 1

The summary of the quantification of two-step coupling products by UV-Vis

| Drug | $C_{drug}$ (mg/mL) | $C_{mAb}$ (mg/mL) | DAR | λ(254) | λ(280) |
|---|---|---|---|---|---|
| APEGA-8 (1ARM + 1ARM) | 0.119 | 0.193 | 22.2 | 0.722 | 0.313 |
| APEGA-9 (4ARM + 1ARM) | 0.184 | 0.186 | 35.6 | 1.226 | 0.505 |
| APEGA-10 (4ARM + 4ARM) | 0.251 | 0.056 | 95.3 | 1.556 | 0.37 |

Example 10: Preparation of Antibody Drug Conjugate (APEGA-11)

(TM-[PEG-1A]-[PEG-2A]-Drug) was prepared from (MAL)3-4ARMPEG5K-NHS (V-3, prepared in Example 1), SH-4ARMPEG5K-(CONH-YSV)3 (prepared in Example 4), Recombinant Anti-HER2 Humanized Monoclonal Antibody (TM), which has a structural formula of:

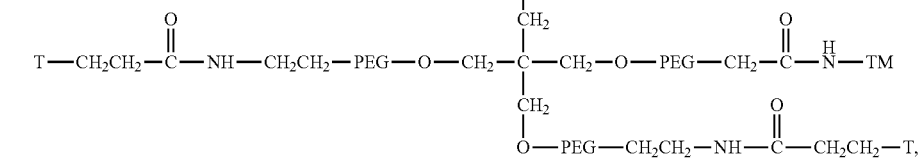

wherein
T is

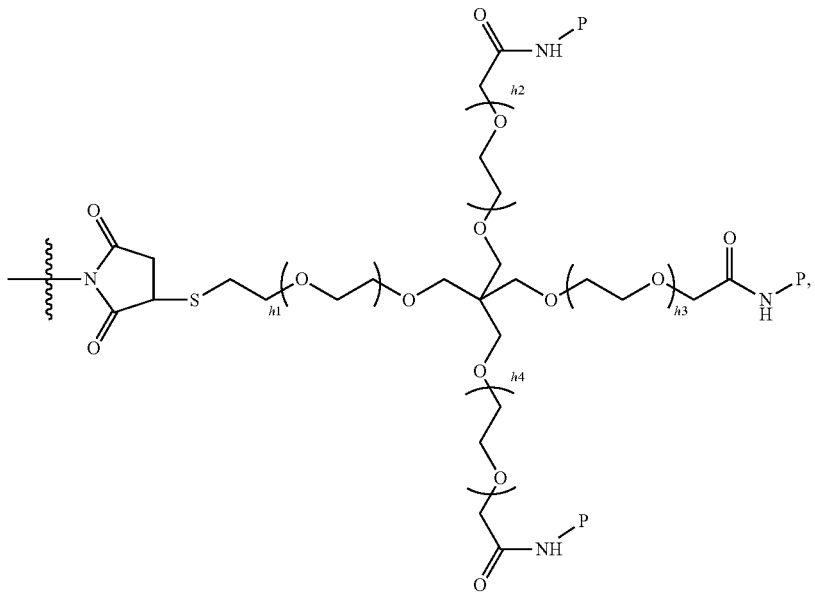

P is tyroservatide, YSV,

TM is a recombinant anti-HER2 humanized monoclonal antibody.

Step 1, preparation of one-step coupling product (PEG1-antibody coupling reactant)

Feed at a molar ratio of antibody:V-3=1:600 (a mass ratio of about 1:2). 358 mg/mL V-3 solution was prepared with 1 mM HCl, and 55.8 μL was quickly added to the antibody coupling buffer system (50 mM sodium phosphate pH 8.0, 50 mM sodium chloride, 1 mM EDTA) (40.3 μL 24.8 mg/mL antibody in 104 μL of coupling buffer), gently shaken at room temperature, react for 2 hours to obtain a one-step coupling product; storage at −20° C. to terminate the reaction.

Step 2, solution replacement

The one-step coupled product was replaced by ultrafiltration to 50 mM sodium phosphate, pH 6.0.

Step 3, two-step coupling

Feed at a molar ratio of the PEG1-antibody coupling reactant:SH-4ARMPEG5K-(CONH-YSV)=1:1, a solution of 20 mg/mL SH-4ARMPEG5K-(CONH-YSV)3 was prepared with 1 mM HCl, and 40 μL was quickly added to the PEG1-antibody coupling reaction solution (80 μL), and gently shaken at room temperature, react for 2 hours; stored at −20° C. to terminate the reaction. The free SH-4ARMPEG5K-(CONH-YSV) 3 molecule was removed by ultrafiltration and the solution was replaced with 50 mM PB, pH 6.0, 97 mM NaCl solution. A further filtration and sterilization was carried out to give a conjugate.

Example 11: Determination of Drug Loading for the Antibody Drug Conjugate in Example 10

Principle:

$$\text{coupling rate} = \frac{C_{drug} \times Mr_{mAb}}{C_{mAb} \times Mr_{drug}}$$

wherein: C(drug) is the concentration of YSV coupled to the Ab in the reaction solution, and is obtained by HPLC subtractive feeding method;

C(Ab) is the concentration of Ab in the reaction solution;

Mr (Ab) is the molecular weight of Ab, 150 KD;

Mr (Drug) is the molecular weight of YSV.

The coupling rate was 97.6 as a result of the determination.

Pharmacokinetics, Pharmacodynamics Experiment

Example 12: Antibody Pharmacokinetic Assay of Antibody Drug Conjugates Prepared in Examples 6, 7, and 8

Experimental method: SD rats were anesthetized by intraperitoneal injection of 40 mg/kg of 1% pentobarbital sodium, and the skin was prepared by the neck and the front of the neck, and disinfected by iodophor. Cut the skin at the right of the neck and expose the jugular vein. After the venous catheter is inserted into the blood vessel, it is ligated and the skin at the opening is sutured. After the end of the operation, about 0.2 mL of the heparin sodium solution and 0.1 mL of the blocking solution were injected into the catheter, and thereafter replaced every day for one week. After one week, the surgical wounds of the rats were all healed, the catheter was fixed, and the blood was taken repeatedly to be used for the pharmacokinetic study of this project. Recombinant anti-HER2 humanized monoclonal antibody (hereinafter abbreviated as Ab) and APEGA-8, 9, 10 (prepared in Examples 6-8, respectively) were administered via the tail vein, respectively, and the blood was taken from the animals at a predetermined time after administration, to perform an analysis.

100 μL/well of 0.05 μg/mL human HER2 protein was coated in microwells with 0.05 M carbonate buffer and incubated overnight at 4° C. Wash the plate with 400 μL PBST, add 300 μL of blocking solution, block at 37° C. for 1 h, and wash the plate with 400 μL of PBST. 100 μL/well of the standard and the sample to be tested were added to the above-mentioned coated reaction wells, and incubated at 37° C. for 1 hour. Then wash. Add an enzyme-labeled antibody: 100 μL/well of goat anti-human IgG enzyme-labeled antibody was added to each reaction well. Incubate for 1 hour at 37° C. and wash. Add substrate liquid to develop: Add 50 μL/well of the temporarily prepared TMB substrate solution to each reaction well at 37° C. for 15-30 minutes. Reaction termination: 50 μL/well of 2 M sulfuric acid was added to each reaction well. The absorbance was measured at 450 nm on an ELISA detector. The linear regression of the standard absorbance value corresponding to the absorbance value (subtracting the blank) was performed, and the regression equation is obtained; the absorbance value of the product to be inspected (subtracting the blank) is incorporated into the standard curve equation to obtain the antibody concentration in the sample to be tested.

Figure 1:
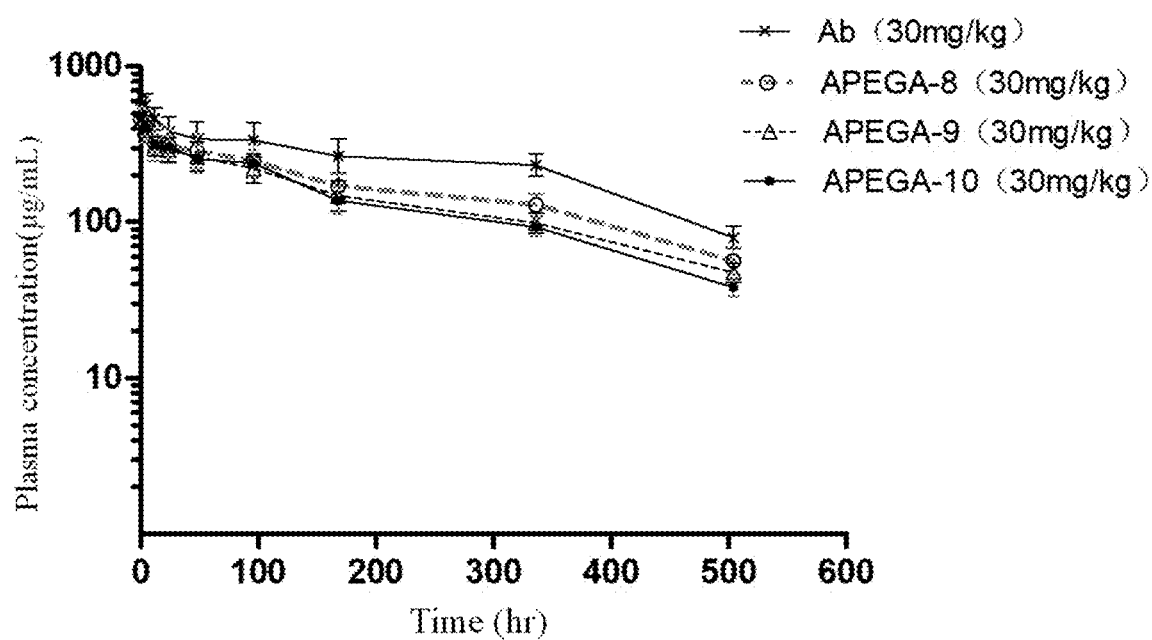
FIG. 1 is a graph of rat plasma drug-time profiles (total antibody concentration, g/mL Vs time, hr), intravenous injection dose of Ab and antibody conjugate 30 mg/kg.

The Experimental results were shown in FIG. 1.

The results showed that the elimination rate of APEGA-8, APEGA-9 and APEGA-10 in rat plasma increased to a certain extent compared with the control Ab, but the decline trend was not significant.

Example 13: Irinotecan Pharmacokinetic Test of Antibody Drug Conjugate Prepared in Example 7

Experimental method: SD rats were anesthetized by intraperitoneal injection of 40 mg/kg of 1% pentobarbital sodium, and the skin was prepared by the neck and the front of the neck, and disinfected by iodophor. Cut the skin at the right of the neck and expose the jugular vein. After the venous catheter is inserted into the blood vessel, it is ligated and the skin at the opening is sutured. After the end of the operation, about 0.2 mL of the heparin sodium solution and 0.1 mL of the blocking solution were injected into the catheter, and thereafter replaced every day for one week. After one week, the surgical wounds of the rats were all healed, the catheter was fixed, and the blood was taken repeatedly to be used for the pharmacokinetic study of this project. Ab, APEGA-9 (prepared in Example 47) and PEG5K-PEG3.5K-Iri (hereinafter abbreviated as PEG-Irinotecan, prepared in Example 45) were administered via the tail vein, respectively, and the blood was taken from the animals at a predetermined time after administration, to perform an analysis.

The assay used a validated HPLC method to detect the content of irinotecan.

Test results were shown in FIG. 2.

The results showed that, compared with PEG-Irinotecan (4.2 mg/kg), the equivalent dose of APEGA-9 after the antibody was conjugated slowed the elimination of irinotecan in plasma over time. The terminal elimination half-life of APEGA-9 was significantly longer than that of PEG-Irinotecan. It is suggested that APEGA-9 elimination rate is significantly slower than PEG-Irinotecan, and the amount of irinotecan exposed to plasma is significantly higher than PEG-Irinotecan.

Example 14: Efficacy Test of Antibody Drug Conjugate Prepared in Examples 6, 7, and 8

Experimental method: Evaluation of the efficacy of the sample was performed using a colorectal cancer model in which HER2 was not expressed. The cell line at logarithmic growth phase was inoculated subcutaneously into the right side of the immunodeficient mice, and the cell inoculation amount was 5×10⁶ cells/mouse. After the transplanted tumor was formed, allow it grow in the mice for 2 passage before use. The tumor tissue with strong growth period was cut into tumor pieces with a diameter of about 2 mm, and inoculated subcutaneously into the right torso of nude mice under sterile conditions. The formed tumor tissue is measured by a vernier caliper, and the long and short diameters are represented by a and b, respectively, and the tumor volume (TV) is calculated as: TV=½×a×b². Animals were randomized after tumor growth to 100-150 mm³. Both models were divided into vehicle group, control group (recombinant anti-HER2 humanized monoclonal antibody Ab, 30 mg/kg) and test group I (administered with APEGA-8, 9, 10, respectively (prepared in Example 6-8), the dose was 30 mg/kg in terms of Ab, and the test group II (PEG-Irinotecan (prepared in Example 5), the dose was 30 mg/kg). Both the test article and the control drug were administered once a week vial the tail vein for a total of three administrations. The diameter of the transplanted tumor was measured twice a week during the entire experiment, and the body weight of the mice was weighed. After the end of the administration, continue to observe the animals for a week, and then they were sacrificed.

Experimental results: The test results were shown in FIG. 3 and Table 2.

TABLE 2

Comparison of tumor inhibition rates in the third week of administration of test articles in colorectal cancer model (HCT-116)

| Test article | Drug loading (based on irinotecan, mg/kg) | Tumor inhibition rate (%) |
|---|---|---|
| Vehicle | / | 0 |
| Ab 30 mg/kg QW×3 | / | −11.7 |
| APEGA-8 (1ARM + 1ARM) 30 mg/kg QW × 3 | 2.6 | 40.1 |
| APEGA-9 (4ARM + 1ARM) 30 mg/kg QW × 3 | 4.2 | 49.5 |
| APEGA-10 (4ARM + 4ARM) 30 mg/kg QW × 3 | 11.2 | 81.7 |
| PEG-Irinotecan 30 mg/kg QW × 3 | 30 | 36.7 |

The results showed that the antitumor activities of the tested APEG-8, APEGA-9 and APEGA-10 increased with the drug loading, and APEGA-10 had stronger anticancer activity; the antibody control did not show antitumor activity. In the case that the dose of irinotecan was lower than that of group II, the efficacy of group I (APEG-8, APEGA-9 and APEGA-10, at a dose of 2.6, 4.2, 11.2 mg/kg, respectively) was still better than group II (PEG-Irinotecan, at a dose of 30 mg/kg). During the whole experiment, no obvious abnormal responding of the animals was observed, and the tolerance to the drugs was good.

The invention claimed is:

1. A ligand drug conjugate, having a structure represented by general formula I:

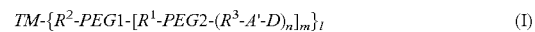

wherein:
TM is a recombinant anti-HER2 humanized monoclonal antibodies;
PEG1 is a multi-branched polyethylene glycol residue having a structure represented by general formula (V-1):

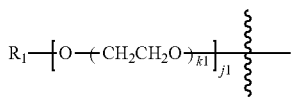
(V-1)

wherein: k1 is an integer from 1 to 240, j1 is an integer from 3 to 8, $R_1$ is a core molecule of a multi-branched polyethylene glycol, and $R_1$ is pentaerythritol;

PEG2 is a multi-branched polyethylene glycol residue having a structure represented by general formula (V-2):

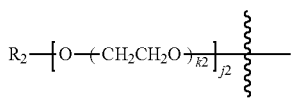
(V-2)

wherein: k2 is an integer from 1 to 240, j2 is an integer from 3 to 8, $R_2$ is a core molecule of multi-branched polyethylene glycol, and $R_2$ is pentaerythritol;

l is an integer from 11 to 100;

m is an integer from 1, 3, 5 or 7;

n is an integer from 1, 3, 5 or 7;

A' is a valine residue;

$R^1$ is a linking unit linking PEG1 and PEG2;

$R^2$ is a ligand unit linking the ligand unit and PEG1;

$R^3$ is a linking unit linking PEG2 and spacer A' or a drug; and

D is irinotecan, or a pharmaceutically acceptable salt thereof;

wherein $R^1$ has a structure of -$A_1$-B-$A_2$-, wherein $A_1$ is selected from the group consisting of: —$(CH_2)_i$NHCO—;

$A_2$ is selected from the group consisting of: —$(CH_2)_i$—;

B is selected from a structure of:

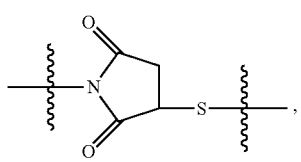

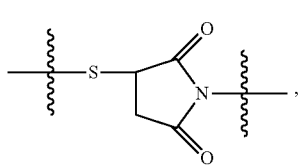

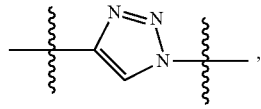

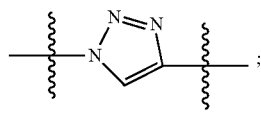

$R^2$ is selected from the group consisting of: —$(CH_2)_i$NHCO— and —$(CH_2)_i$CONH;

$R^3$ is selected from the group consisting of: —$(CH_2)_i$CO—;

i is an integer from 0 to 10.

2. The ligand drug conjugate or a pharmaceutically acceptable salt thereof according to claim 1, wherein the PEG1 and/or PEG2 have a molecular weight of from 1 to 50 kDa.

3. The ligand drug conjugate or a pharmaceutically acceptable salt thereof according to claim 1, wherein the ligand drug conjugate has a structure represented by formula VIII:

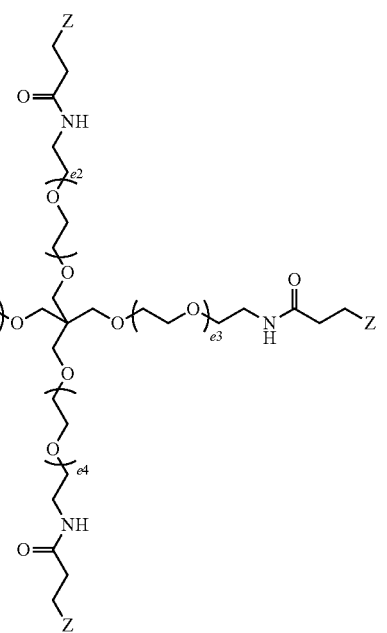
(VIII)

Z is

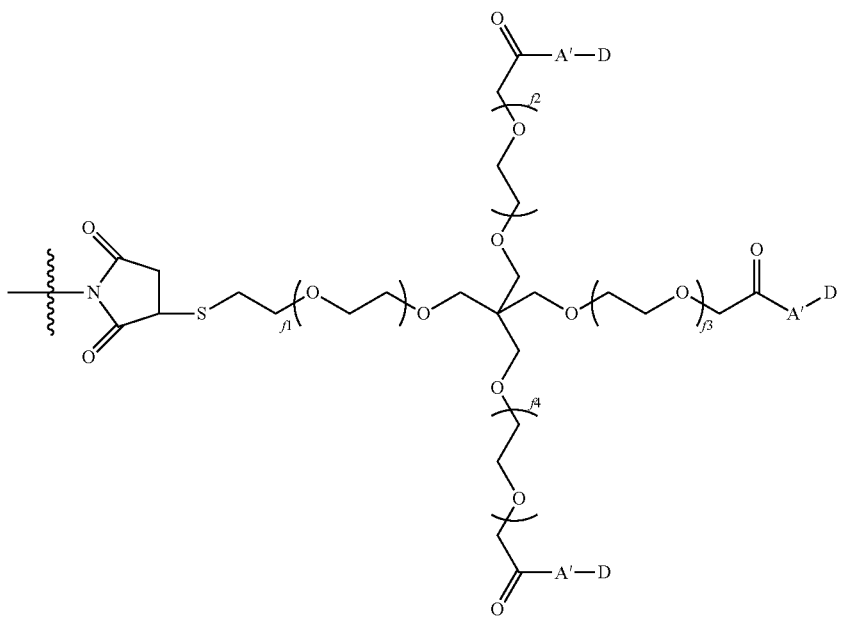

wherein e1 to e4 and f1 to f4 are independently selected from an integer of 1-240;
-A'-D has a structure of:

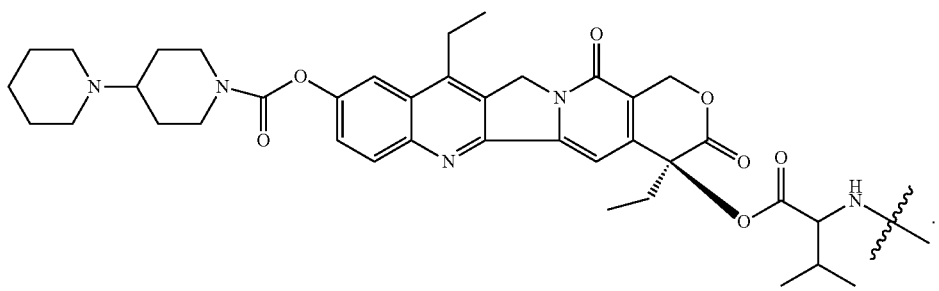 [SMILES: *NC(C(=O)O[C@]1(CC)C(=O)OCc2c1cc1n(c2=O)Cc2c-1nc1ccc(OC(=O)N3CCC(N4CCCCC4)CC3)cc1c2CC)C(C)C]

4. The ligand drug conjugate or a pharmaceutically acceptable salt thereof according to claim 1, wherein the pharmaceutically acceptable salt is one or more selected from the group consisting of sodium salt, potassium salt, cesium salt, calcium salt, magnesium salt, triethylamine salt, pyridine salt, methylpyridine salt, ethanolamine salt, triethanolamine salt, dicyclohexylamine salt, N,N-dibenzylethylenediamine salt, hydrochloride, hydrobromide, sulfate, nitrate, phosphate, formate, acetate, trifluoroacetate, pantothenate, succinate, citrate, tartrate, fumarate, maleate, gluconate, glucuronate, saccharate, benzoate, lactate, methanesulfonate, ethanesulfonate, besylate, p-toluenesulfonate, argininate, aspartate, glutamate, pantothenate, and ascorbate.

5. A pharmaceutical composition comprising a ligand drug conjugate or a pharmaceutically acceptable salt thereof according to claim 1, and a pharmaceutically acceptable carrier or excipient.

* * * * *